(12) United States Patent
Kukkola

(10) Patent No.: US 6,599,942 B1
(45) Date of Patent: Jul. 29, 2003

(54) THYROMIMETIC ORGANIC COMPOUNDS

(75) Inventor: Paivi Janna Kukkola, Whitehouse Station, NJ (US)

(73) Assignee: Novartis AG, Basel (CH)

( * ) Notice: Subject to any disclaimer, the term of this patent is extended or adjusted under 35 U.S.C. 154(b) by 36 days.

(21) Appl. No.: 09/696,502

(22) Filed: Oct. 25, 2000

Related U.S. Application Data

(63) Continuation of application No. 09/533,219, filed on Mar. 23, 2000.
(60) Provisional application No. 60/183,030, filed on Mar. 29, 1999.

(51) Int. Cl.[7] .................. A61K 31/195; A61P 9/10; C07C 229/00; C07C 239/00
(52) U.S. Cl. ............. 514/563; 514/535; 514/617; 560/19; 560/143; 562/433; 564/155
(58) Field of Search ................ 514/535, 563, 514/617; 560/19, 143; 562/433; 564/155

(56) References Cited

U.S. PATENT DOCUMENTS

| | | | |
|---|---|---|---|
| 4,396,418 A | 8/1983 | Schirmer et al. | 71/98 |
| 4,540,578 A | 9/1985 | Chou et al. | 514/349 |
| 5,284,971 A | 2/1994 | Walker et al. | 562/429 |
| 5,401,772 A | 3/1995 | Yokoyama et al. | 514/539 |
| 5,776,951 A | 7/1998 | Arrowsmith et al. | 514/328 |
| 6,326,398 B1 * | 12/2001 | Chiang et al. | 514/535 |

FOREIGN PATENT DOCUMENTS

| | | |
|---|---|---|
| EP | 067 381 B1 | 12/1982 |
| EP | 524 781 B1 | 1/1993 |
| EP | 580 550 B1 | 1/1994 |
| EP | 647 612 A1 | 4/1995 |
| EP | 1 033 364 A1 | 9/2000 |
| WO | WO 94/26737 | 11/1994 |
| WO | WO 96/10023 | 4/1996 |
| WO | WO 97/21993 | 6/1997 |
| WO | WO 00/07972 | 2/2000 |
| WO | WO 00/51971 | 9/2000 |

OTHER PUBLICATIONS

Matsubara et. al., Chemical Abstract, 1993, vol. 119, Abstract #46724.*
Steele R.E. et al., "CGS 26214, the Thyroxine Connection Revisted", Atherosclerosis X, pp. 321–324 (1995).
Taylor A.H. et al., "P2–1001—Effect of a Novel Thromimetic, CGS 23425 on Lipoprotein Metabolism", The Endocrine Society, p. 655, (1996).
Taylor A.H. et al., "Beneficial Effects of a Novel Thyromimetic on Lipoprotein Metabolism", Molecular Pharmacology, pp. 542–549 (1997).
Chemical Abstracts 130:291600 (1999).
Derwent Abstract 99–266950/23 of JP 11080107–A Mar. 26, 1999.
Chemical Abstracts 1995:582559 CAPLUS (WO 94/26737).
Chemical Abstracts 1996:451993 CAPLUS (WO 96/10023).
Chemical Abstracts 130:291600 (1999).
Derwent Abstract 99–266950/23 of JP 11080107–A Mar. 26, 1999.
Stanton J.L. et al., Bioorganic & Medical Chemistry Letters, vol. 10, pp. 1661–1663 (2000).
Stephan Z.F. et al., Atherosclerosis, vol. 126, pp. 53–63 (1996).
Steele, R.E. et al., Atherosclerosis X, pp. 321–324 (1995).
Taylor A.H. et al., The Endocrine Society, Abstract P2–1001, ICE'96, p. 655 (1996).
Taylor A.H. et al., Molecular Pharmacology, vol. 52, pp. 542–547 (1997).
Yokoyama N. et al., J.Med.Chem., vol. 38, pp. 695–707 (1995).

* cited by examiner

Primary Examiner—Mukund J. Shah
Assistant Examiner—Tamthom N. Truong
(74) Attorney, Agent, or Firm—Norbert Gruenfeld

(57) ABSTRACT

Compounds of the formula

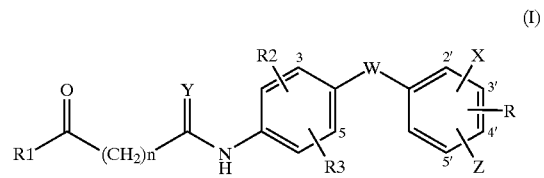

(I)

in which W is O, S, S(O) or S(O)$_2$; X is —SR4, —S(O)R4, or —S(O)$_2$R4, —S(O)$_2$NR5R6; or X is —C(O)NR5R6 provided that —C(O)NR5R6 is located at the 3', 4' or 5' position; Y is O or H$_2$; Z is hydrogen, halogen, hydroxy, optionally substituted alkoxy, aralkoxy, acyloxy or alkoxycarbonyloxy; R is hydrogen, halogen, trifluoromethyl, lower alkyl or cycloalkyl; R1 is hydroxy, optionally substituted alkoxy, aryloxy, heteroaryloxy, aralkyloxy, cycloalkoxy, heteroaralkoxy or —NR5R6; R2 is hydrogen, halogen or alkyl; R3 is halogen or alkyl; R4 is optionally substituted alkyl, aryl, aralkyl, heteroaralkyl or heteroaryl; R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring; n represents zero or an integer from 1 to 4; pharmaceutically acceptable salts thereof; pharmaceutical compositions comprising said compounds; a method to prevent and treat diseases associated with an imbalance of thyroid hormones, such as hypo- and hyperthyroidism, obesity, osteoporosis and depression; and, a method of lowering LDL cholesterol and Lp(a) levels in mammals using such compounds.

22 Claims, No Drawings ures

THYROMIMETIC ORGANIC COMPOUNDS

This application is a continuation of application Ser. No. 09/533,219 filed Mar. 23, 2000, which in turn claims the benefit of provisional Application No. 60/183,030 filed Mar. 29, 1999 (converted from application Ser. No. 09/280,105).

SUMMARY OF THE INVENTION

The present invention relates to novel compounds of formula I (I)

in which

W is O, S, S(O) or S(O)$_2$;

X is —SR4, —S(O)R4, —S(O)$_2$R4, or —S(O)$_2$NR5R6; or X is —C(O)NR5R6 provided that —C(O)NR5R6 is located at the 3'-, 4'- or 5'-position;

Y is O or H$_2$;

Z is hydrogen, halogen, hydroxy, optionally substituted alkoxy, aralkoxy, acyloxy or alkoxycarbonyloxy;

R is hydrogen, halogen, trifluoromethyl, lower alkyl or cycloalkyl;

R1 is hydroxy, optionally substituted alkoxy, aryloxy, heteroaryloxy, aralkoxy, cycloalkoxy, heteroaralkoxy or —NR5R6;

R2 is hydrogen, halogen or alkyl;

R3 is halogen or alkyl;

R4 is optionally substituted alkyl, aryl, aralkyl, heteroaralkyl or heteroaryl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring;

n represents zero or an integer from 1 to 4; and pharmaceutically acceptable salts thereof.

The compounds of the invention are thyromimetic agents which can be used to prevent and/or treat diseases associated with an imbalance of thyroid hormones, such as hypo- and hyper-thyroidism, obesity, osteoporosis and depression. The compounds of the invention are, in particular, hypolipedemic agents which enhance the clearance of cholesterol from circulation, particularly the clearance of cholesterol in the form of low density lipoproteins (LDL). They, inter alia, upregulate hepatic LDL receptor function in mammals. Thus, they are useful for reducing total cholesterol plasma levels in mammals, in particular for reducing levels of LDL-cholesterol. Furthermore, such compounds also lower elevated lipoprotein (a) [Lp(a)] levels, an independent cardiovascular risk factor, in mammals. The compounds of the invention can therefore be used for the prevention and/or treatment of occlusive cardiovascular conditions in which hyperlipidemia and hyperlipoproteinemia are implicated, such as atherosclerosis and coronary heart disease in mammals.

DETAILED DESCRIPTION OF THE INVENTION

The present invention provides for compounds of formula I, pharmaceutical compositions comprising such compounds and for methods of using such compounds.

Listed below are definitions of various terms used to describe the compounds of the instant invention. These definitions apply to the terms as they are used throughout the specification (unless they are otherwise limited in specific instances either individually or as part of a larger group).

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpenthyl, octyl and the like. Substituted alkyl groups include, but are not limited to, alkyl groups substituted by one or more (e.g. two or three) of the following groups: halo, lower alkenyl, hydroxy, cycloalkyl, alkanoyl, alkoxy, alkyloxyalkoxy, alkanoyloxy, amino, alkylamino, dialkylamino, dialkylaminocarbonyl, alkanoylamino, thiol, alkylthio, alkylthiono, alkylsulfonyl, arylsulfonyl, heteroarylsulfonyl, sulfonamido, nitro, cyano, carboxy, alkoxycarbonyl, aryl, aralkyl, aralkoxy, guanidino, heterocyclyl including indolyl, imidazolyl, furyl, thienyl, thiazolyl, pyrrolidyl, pyridyl, pyrimidyl, piperidyl, morpholinyl and the like. Preferred substituents of substituted alkyl, especially of substituted alkyl of variable R1 being substituted alkoxy, are lower alkyl, cycloalkyl, lower alkenyl, benzyl, mono or disubstituted lower alkyl, e.g. ω-(amino, mono- or di-lower alkylamino, carboxy, lower alkoxycarbonyl)-lower alkyl, α-(lower alkanoyloxy, lower alkoxycarbonyl or di-lower alkylaminocarbonyl)-lower alkyl, such as pivaloyloxymethyl.

The term "lower alkyl" refers to those alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and further containing at least one carbon to carbon double bond. Groups having two to four carbon atoms are preferred.

The term "alkylene" refers to a straight chain bridge of 1 to 6 carbon atoms connected by single bonds (e.g., —(CH$_2$)$_x$— wherein x is 1 to 6), which may be substituted with 1 to 3 lower alkyl groups.

The term "cycloalkyl" refers to cyclic hydrocarbon groups of 3 to 8 carbon atoms.

The term "alkoxy" refers to alkyl-O—.

The term "acyl" refers to alkanoyl, aroyl, heteroaroyl, arylalkanoyl or heteroarylalkanoyl.

The term "alkanoyl" refers to alkyl-C(O)—.

The term "alkanoyloxy" refers to alkyl-C(O)—O—.

The terms "alkylamino" and "dialkylamino" refer to (alkyl)NH— and (alkyl)$_2$N—, respectively.

The term "alkanoylamino" refers to alkyl-C(O)—NH—.

The term "alkylthio" refers to alkyl-S—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "alkyl" as referred to in the above definitions relates to optionally substituted alkyl as defined above.

The term "aryl" refers to monocyclic or bicyclic aromatic hydrocarbon groups having 6 to 12 carbon atoms in the ring portion, such as phenyl, naphthyl, tetrahydronaphthyl, and biphenyl groups, each of which may optionally be substituted by one to four substituents such as alkyl, halo, hydroxy, alkoxy, alkanoyl, alkanoyloxy, amino, alkylamino, dialkylamino, alkanoyl-amino, thiol, alkylthio, nitro, cyano, carboxy, carboxyalkyl, alkoxycarbonyl, alkyl-thiono, alkylsulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkoxy" refers to an aryl group bonded through an alkoxy group.

The term "arylsulfonyl" refers to aryl-$S(O)_2$—.

The term "aroyl" refers to aryl-$C(O)$—.

The term "heterocyclyl" refers to an optionally substituted, fully saturated or unsaturated, aromatic or non-aromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, 2-pyridone, N-lower alkyl-pyridone, e.g. N-lower alkyl-2-pyridone, pyrazinyl, pyrimidinyl, pyridazinyl, tetrahydropyranyl, morpholinyl, thiamorpholinyl, S-oxo-thiamorpholinyl S,S-dioxo-thiamorpholinyl, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl) and the like.

Exemplary tricyclic heterocyclic groups include carbazolyl, benzindolyl, phenanthrolinyl, acridinyl, phenanthridinyl, xanthenyl and the like.

The term "heterocyclyl" includes substituted heterocyclic groups. Substituted heterocyclic groups refer to heterocyclic groups substituted with 1, 2 or 3 of the following:

(a) alkyl;
(b) hydroxy (or protected hydroxy);
(c) halo;
(d) oxo (i.e. =O);
(e) amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfonamido, sulfonamidoalkyl or sulfonamidodialkyl;
(o) aryl;
(p) alkylcarbonyloxy;
(q) arylcarbonyloxy;
(r) arylthio;
(s) aryloxy;
(t) alkylthio;
(u) formyl;
(v) aralkyl; or
(w) aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by one or more substitutents as described in connection with substituted aryl, e.g. by lower alkyl, lower alkoxy or halo.

The term "heterayloxy" refers to heteroaryl-O—.

The term "heteroarylsulfonyl" refers to heteroaryl-$S(O)_2$—.

The term "heteroaroyl" refers to heteroaryl-$C(O)$—.

The term "heteroaralkyl" refer to a heteroaryl group bonded through an alkyl group.

Encompassed by the invention are prodrug derivatives, e.g., any pharmaceutically acceptable prodrug ester derivatives of the carboxylic acids of the invention (COR1 being carboxy) which are convertible by solvolysis or under physiological conditions to the free carboxylic acids.

Examples of such carboxylic acid esters include esters defined by $COR_1$, and are preferably lower alkyl esters, cycloalkyl esters, lower alkenyl esters, benzyl esters, mono or disubstituted lower alkyl esters, e.g. the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxy-methyl ester, and the like conventionally used in the art.

Preferred meanings of R are hydrogen or lower alkyl;

Preferred meanings of R1 are hydroxy, lower-alkoxy or aryloxy.

Preferred meanings of R2 are hydrogen, halogen or lower alkyl.

Preferred meanings of R3 are halogen or lower alkyl.

Preferred meanings of R4 are phenyl or phenyl substituted by one or more substituents selected from the group consisting of lower alkyl, lower alkoxy, halogen and trifluoromethyl.

Preferred meaning of R5 is hydrogen.

Preferred meanings of R6 are phenyl or phenyl substituted by one or more substituents selected from the group consisting of lower alkyl, lower alkoxy, halogen and trifluoromethyl.

Preferred W is O.

Preferred X is —$S(O)_2R4$ or —$S(O)_2NR5R6$

Preferred Y is O.

Preferred Z is hydrogen or hydroxy.

The integer "n" preferably is zero, 1 or 2.

The compounds of the invention depending on the nature of the substituents, may possess one or more asymmetric centers. The resulting diastereoisomers, enantiomers and geometric isomers are encompassed by the instant invention.

Preferred are the compounds of formula I as defined above with the proviso that when X is —C(O)NR5R6, Z is different from hydrogen.

Preferred are the compounds of formula I in which

W is O or S;

X is —S(O)$_2$R4; R4 being lower alkyl, phenyl or phenyl substituted by one or more substituents selected from the group consisting of lower alkyl, lower alkoxy, halogen and trifluoromethyl; or is —S(O)$_2$NR5R6 or is —C(O)NR5R6; R5, in each case, being hydrogen or lower alkyl and R6, in each case, being hydrogen, lower alkyl, lower alkyl substituted by NR5R6, 3- to 7-membered cycloalkyl, phenyl, phenyl substituted by one or more substituents selected from the group consisting of lower alkyl, lower alkoxy, halogen and trifluoromethyl; pyridyl or N-lower alkyl-2-pyridone; or R5 and R6 combined, in each case, being alkylene or alkylene interrupted by O or S(O)$_2$ which together with the nitrogen atom to which they are attached form a 5- to 7-membered ring;

Y is O or H$_2$;

Z is hydrogen or hydroxy;

R is hydrogen;

R1 is hydroxy, lower alkoxy or NR5R6; R5 being hydrogen or lower alkyl and R6 being hydrogen, lower alkyl, lower alkoxy or R5 and R6 combined being alkylene or alkylene interrupted by O which together with the nitrogen atom to which they are attached form a 5- to 7-membered ring;

R2 is hydrogen, halogen or lower alkyl;

R3 is halogen or lower alkyl;

n represents zero, 1 or 2;

with the proviso that when X is —C(O)NR5R6, Z is hydroxy;

and pharmaceutically acceptable salts thereof.

Preferred are the compounds of formula IA

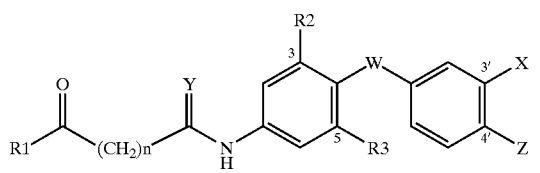

(IA)

in which

W is O or S;

X is —SR4, —S(O)R4, —S(O)$_2$R4, —S(O)$_2$NR5R6 or —C(O)NR5R6;

Y is O or H$_2$;

Z is hydrogen, halogen, hydroxy, alkoxy, aralkoxy, acyloxy or alkoxycarbonyloxy;

R1 is hydroxy, lower alkoxy or aryloxy;

R2 is hydrogen, halogen or lower alkyl;

R3 is halogen or lower alkyl;

R4 is optionally substituted alkyl, aryl, aralkyl, heteroaryl or heteroaralkyl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring;

n represents zero, 1 or 2;

and pharmaceutically acceptable salts thereof.

Further preferred are the compounds of formula IB

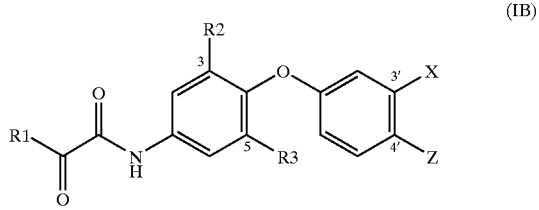

(IB)

in which

X is —S(O)$_2$R4, —S(O)$_2$NR5R6 or —C(O)NR5R6;

Z is hydroxy, lower alkanoyloxy or lower alkoxy;

R1 is hydroxy or lower alkoxy;

R2 and R3 are lower alkyl;

R4 is aryl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring; and pharmaceutically acceptable salts thereof.

Preferred are compounds of formula I, IA and IB, and pharmaceutically acceptable salts thereof, wherein X is —S(O)$_2$R4 or —S(O)$_2$NR5R6.

Most preferred are the compounds of formula IC

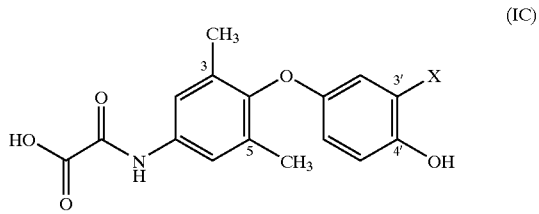

(IC)

in which

X is —S(O)2R4 or —S(O)$_2$NR5R6;

R4 is monocyclic aryl;

R5, R6 and R7 are independently hydrogen, optionally substituted alkyl or aryl; or R5 and R6 combined are CH$_2$CH$_2$—Q—CH$_2$CH$_2$ wherein Q is CH$_2$, O, NR7, S, S(O) or S(O)$_2$ which together with the nitrogen atom to which they are attached from a 6-membered ring; pharmaceutically acceptable prodrug esters thereof; and pharmaceutically acceptable salts thereof.

Particularly preferred are the compounds of formula IC wherein X is S(O)$_2$R4 and R4 is phenyl optionally substituted by lower alkyl, halo, lower alkoxy or trifluoromethyl; pharmaceutically acceptable salts thereof; and prodrug derivatives thereof.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic, and organic sulfonic acids e.g. hydrochloric acid, methanesulfonic acid, maleic acid, are possible provided a basic group, such as pyridyl, constitutes part of the structure.

Compounds of formula I may be prepared from appropriately substituted phenols of formula II

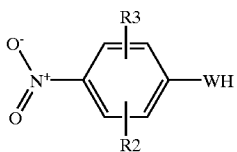
(II)

wherein R2 and R3 have meaning as defined herein and W is oxygen (prepared according to methods well-known in the literature) by first converting such to e.g. a trifluoromethylsulfonyl ester, and treating the latter with lithium chloride in an inert solvent such as N-methyl-pyrrolidone, N,N-dimethylformamide or dimethylsulfoxide to form compounds of formula III

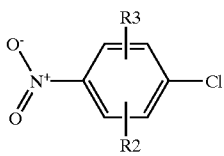
(III)

Compounds of formula III can be converted to compounds of formula IV

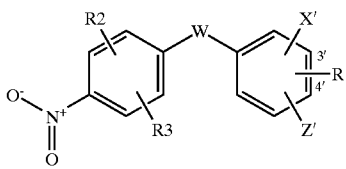
(IV)

by reaction with appropriately substituted phenols or thiophenols of formula V

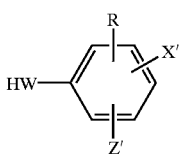
(V)

wherein R has meaning as defined herein, X' and Z' represent X and Z as defined herein, or X' and Z' are groups convertible to X and Z respectively, in the presence of a base such as sodium hydride or potassium carbonate in an inert solvent such as N-methylpyrrolidone, N,N-dimethylformamide or dimethylsulfoxide at ambient or elevated temperature. Compounds of formula V can be obtained using methodologies described herein or in the art.

Alternatively, compounds of formula IV can be obtained by condensing bis-aryl iodonium tetrafluoroborates of formula VI

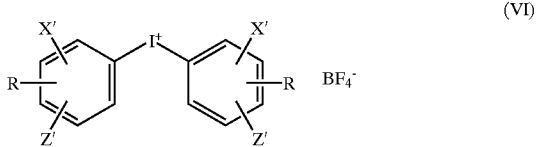
(VI)

in which R, X' and Z' are as defined above, with phenols or thiophenols of formula II wherein W is oxygen or sulfur as described in the art, e.g., in the presence of a copper catalyst and a base such as triethylamine in an inert solvent such as dichloromethane.

Compounds of formula IV wherein Z' is alkoxy or aralkoxy can be converted to compounds of formula IV wherein Z' is hydroxy according to methods well-known in the art, e.g. using acid such as hydrobromic acid or a boron trihalide, such as boron trichloride or boron tribromide when Z' is in particular a methoxy group or using hydrogen in the presence of a catalyst such as palladium on carbon when Z' is in particular a benzyloxy group.

Compounds of the invention wherein X is S(O)$_2$NR5R6 may be prepared by, for example, first treating compounds of formula IV, wherein R and X' are hydrogen and X' is located at the 3' position, and Z' is hydroxy, alkoxy or aralkoxy and Z' is located at the 4' position, with chlorosulfonic acid in an organic solvent such as dichloromethane to produce compounds of formula VII

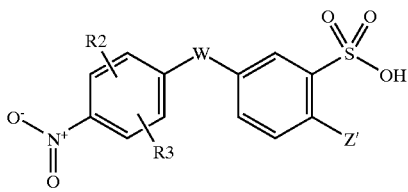
(VII)

wherein Z' is as defined above. Compounds of formula VII in which Z' is hydroxy, may be converted to compounds of formula VII wherein Z' is a protected hydroxyl group such as alkanoyloxy, alkoxycarbonyloxy or trialkylsiloxy using methods and conditions well-known in the art.

Compounds of formula VII wherein Z' is alkoxy, aralkoxy, alkanoyloxy, alkoxycarbonyloxy or trialkylsiloxy can be converted to compounds of formula VIII

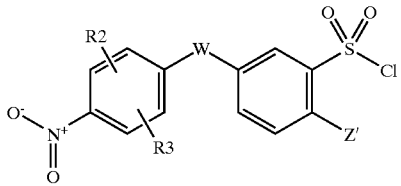
(VIII)

wherein Z' is as defined above by reaction with a chlorinating agent such as oxalyl chloride or thionyl chloride in an inert solvent such as dichloromethane or tetrahydrofuran in the presence of a catalytic amount of N,N-dimethylformamide.

A reaction of compounds of formula VIII with primary or secondary amines of formula R5R6NH wherein R5 and R6 are as defined herein in the presence of a base such as N-methyl-morpholine or triethylamine in an organic solvent such as dichloromethane affords compounds of formula IX

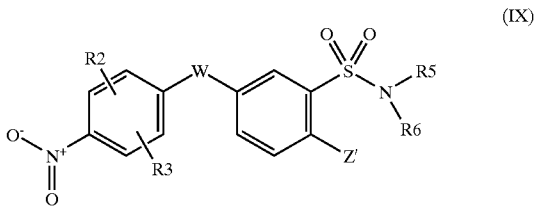

(IX)

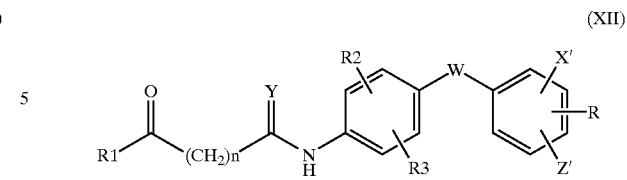

(XII)

Compounds of formula IX wherein Z' is as defined above can be converted to compounds of formula IX wherein Z' is hydroxy using methods and conditions well-known in the art or as illustrated herein.

Conversion of nitro substituted compounds of formula IV, for example those of formula IX, to amines of e.g. formula X

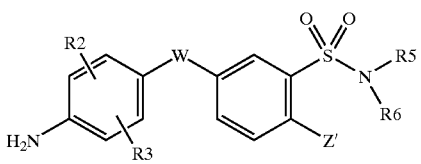

(X)

can be achieved according to methods described in the art, e.g. with hydrogen in the presence of a catalyst such as palladium on carbon in a polar solvent such as ethanol or tetrahydrofuran.

Any resulting amines, for example those of formula X, can be treated with acylating agents such as ethyl oxalyl chloride, ethyl malonyl chloride, ethyl succinyl chloride or ethyl bromoacetate in the presence of a base such as N-methylmorpholine or triethylamine in an organic solvent such as dichloromethane, tetrahydrofuran or N,N-dimethylformamide to form compounds of formula I, e.g. those of formula XI

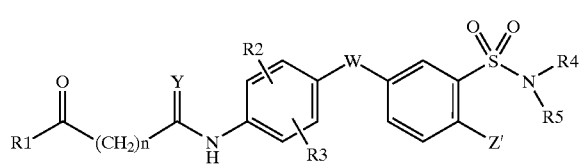

(XI)

wherein R1 is alkoxy, Y is oxygen or $H_2$, Z' represents Z as defined herein or Z' is a group convertible to Z and n represents an integer from zero to four. Compounds of formula I wherein R1 is alkoxy can also be prepared by condensing e.g. compounds of formula X with acylating agents such as dimethyl or diethyl oxalate at elevated temperature using the acylating agent both as a reagent and a solvent.

Compounds of formula I wherein R1 is e.g. alkoxy or aryloxy can be hydrolyzed to compounds of formula I wherein R1 is hydroxy according to conventional methods, e.g. using an aqueous base such as an alkali metal carbonate or hydroxide in an organic solvent such as ethanol or tetrahydrofuran.

Similarly, other compounds of formula IV wherein, X' and Z' represent X and Z as defined herein or X' and Z' are groups convertible to X and Z respectively are converted to compounds of formula XII in a manner illustrated herein or by modifications thereof and, if necessary, said compounds are converted to the corresponding compounds of formula I, by converting X' and Z' to X and Z respectively. For example, compounds wherein X'=COOH are converted to the corresponding amides of formula I wherein X is C(O)NR5R6 according to methods well known in the art. Similarly compounds wherein $COR_1$ is COOH can be converted to compounds wherein $COR_1$ is $CONR_5R_6$.

The starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, N.Y., 1973, T. W. Greene, "Protective Groups in Organic Synthesis", Wiley, N.Y., 1991.

In the processes cited herein, reactive functional derivatives of carboxylic acids represent, for example, anhydrides (especially mixed anhydrides), acid halides, acid azides, lower alkyl esters, and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, for the treatment of diseases associated with an imbalance of thyroid hormones, such as hypo- and hyperthyroidism, obesity, osteoporosis, depression, and in particular for the treatment and/or pre-vention of occlusive cardiovascular conditions in which hyperlipidimia and hyperlipoproteinemia are implicated, comprising an effective amount of a pharmacologically active compound of the inventon, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

A unit dosage for a mammal of about 50 to 70 kg may contain between about 0.01 mg and 10 mg of the active ingredient. The dosage of active compound is dependent on the species of warm-blooded aninial (mammal), the body weight, age and individual condition, on the form of administration, and on the compound involved.

The problem solved by the present invention is to provide pharmacologically potent hypolipidemic agents which reduce plasma cholesterol levels in mammals. The compounds of the invention demonstrate potent binding to the triiodothyronine ($T_3$) nuclear receptor which is indicative of upregulation of LDL receptor activity and enhancement of the clearance of LDL-cholesterol from the circulation. The compounds of the invention are thus particularly useful in mammals as hypocholesteremic agents for the treatment and prevention of occlusive cardiovascular conditions in which hypercholesteremia is implicated, by reducing plasma levels of total and LDL-cholesterol. The invention furthermore relates to the use of the compounds according to the invention for the preparation of medicaments, in particular of medicaments useful for the treatment and prevention of occlusive cardiovascular conditions in which hypercholestermia is implicated, by reducing plasma levels of total and LDL-cholesterol.

Compounds of the invention also reduce lipoprotein (a) levels and are thus useful for the treatment and prevention of occlusive cardiovascular conditions in which Lp(a) is implicated.

Selective thyromimetic hypolipidemic agents of the invention which are substantially free of undesirable cardiac side effects associated with thyroid hormones are preferred.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-7}$ molar and $10^{-11}$ molar concentrations. The dosage in vivo may range depending on the route of administraton, between about 0.1 and 1000 micrograms/kg, preferably between about 0.5 and 300 micrograms/kg, advantageously between about 1 and 100 micrograms/kg.

The compounds of the invention bind to the triodoethyronine ($T_3$) receptor and are thus useful as thyroid hormone agonists in mammals.

The in vitro binding to $T_3$ nuclear receptors is determined as follows:

Rat liver nuclei and plasma membrane preparations are obtained from Sprague-Dawley (CD) rats (Charles River Labs.) by differential centrifugation as described by Emmelot at al (Methods in Enzymology 31:75, Part A, 1974) with minor modificatons. The nuclear fraction obtained from the 275× g pellet is further purified as generally described by Spindler et al (J. Biol. Chem. 250:4118, 1975).

The novel test compounds are assayed for binding to the nuclei by the method of Spindler et al (J. Biol. Chem. 250:4118, 1975). The nuclei are incubated at 22° C. with 0.3 nM of [$^{125}$I]-L-triiodothyronine (L-$T_3$). Parallel incubations are conducted with tubes containing, in addition to the nuclei and radioactive L-$T_3$, either various concentrations of the test compounds or 3 µM of nonradioactive L-$T_3$. The latter is used as a measure of nonspecific binding. The radioactivity bound to the nuclei is determined following centrifugation of the reaction mixture at 800× g for 7 minutes and washing of the pellet obtained. The amount of [$^{125}$I]-L-$T_3$ specifically bound is determined by subtracting the amount nonspecifically bound (radioactivity contained in the nuclear pellet following incubation with excess (3 µM) non-radioactive L-$T_3$. The concentration of test compound which inhibits the specific binding of [$^{125}$I]-L-$T_3$ by 50 percent ($IC_{50}$) is determined graphically from the reciprocal plot of the specifically bound [$^{125}$I]-L-$T_3$ versus the various concentrations of the test compound.

Cholesterol lowering activity is determined in the rat as follows:

Male Sprague-Dawley rats (230–250 g) (Taconic Farms) are maintained ad libitum on water and a high cholesterol diet (1.5% cholesterol and 0.5% cholic acid) for two weeks prior to and during the 7-day treatment period. Groups of animals are treated orally by gavage with the vehicle alone or with test compound for 7 consecutive days. After the last dose, animals are fasted for 18 hours and blood is collected. Blood samples are centrifuged at 2500 rpm for 10 minutes to prepare plasma for total cholesterol determination as well as LDL and HDL cholesterol concentrations. HDL values are determined after LDL/VLDL precipitation (Warnick and Albers, 1978). All samples are analyzed enzymatically for cholesterol with a diagnostic reagent kit (Sigma Chemical Co., St. Louis, Mo.). The analysis is performed on a Bio-Mek automated work station. LDL/VLDL fractions are precipitated in the following manner: 0.35 mL of plasma is aliquoted into Eppendorf tubes to which 12 µL of 2M manganese chloride, 11.2 µL of sodium heparin (Porcine Intestinal, 5000 units/mL), and 8.3 µL of normal saline are added. The samples are vortexed and are placed on ice for 15 minutes, then centrifuged at 4° C. for 10 minutes at 1300 rpm and the supernatant is enzymatically analyzed for cholesterol. The HDL cholesterol concentration is adjusted for dilution by multiplying the supernatant cholesterol value by 1.09. LDL/VLDL cholesterol values are obtained by subtracting HDL cholesterol from total cholesterol.

Cholesterol lowering activity can also be evaluated in normocholesterolemic dogs fed regular chow following the procedure described above, by administration of test compound orally for 5 days.

Cholesterol and Lp(a) lowering activity can be determined in the normolipemic cynomolgus monkey as follows:

Adult male and female cynomolgus monkeys (Macaca fascicularis) weighing 3–7 kg are used. Animals are individually housed and fed a standard monkey chow diet (Purina 5047) supplemented with fresh fruits and vegetables. Each animal serves as its own control and each dosing regime is followed by a wash out period. Test compounds were dissolved in ethanol, imbibed in fruit pulp and administered orally. Animals are dosed once a day with test compounds for a treatment period varying from 8 to 28 days. Blood samples are obtained after an overnight fast at baseline and at the end of the study. Blood samples (3 ml) are collected into Vacutainer tubes (containing EDTA) from the femoral vein of mechanically restrained non-sedated animals. Blood is centrifuged at 2000 rpm for 20 min at 4° C. Plasma samples are divided into aliquots and stored at −70° C. until analyzed. Plasma concentrations of total cholesterol (TC) and triglycerides (TG) are determined by enzymatic methods using commercial kits (Sigma Diagnostics). High-density lipoprotein cholesterol (HDL-C) concentration is measured after precipitation of apoB-containing lipoproteins. Since the fasting plasma of cynomolgus monkeys on a chow diet contains negligible amounts of cholesterol in very low-density lipoprotein, the low-density lipoprotein cholesterol (LDL-C) concentration is calculated by subtracting HDL-C from TC. The assays are performed in 96-well microtiter plates, which are read in a microplate spectrophotometer (Dynatech MR 5000). Plasma concentrations of Lp(a) are determined by a commercial Lp(a) ELISA (PerImmune, Inc.) using the kit controls and reference Lp(a) standard. The Lp(a) ELISA employs a monoclonal antibody against apolipoprotein(a) for capture and a polyclonal antibody against apolipoprotein B for detection. The assay is specific for Lp(a) and does not measure free apo(a), apoB or plasminogen. Quantification of Lp(a) is not affected by apo(a) size. The Lp(a) plasma concentration is reported as milligrams of total Lp(a) mass. Samples from each study are assayed in a single run.

Illustrative of the invention, the compound of example 26 demonstrates an $IC_{50}$ of about 0.17 nM, the compound of example 28 demonstrates an $IC_{50}$ of about 0.13 nM, the compound of example 35 demonstrates an $IC_{50}$ of about 1.00 nM and the compound of example 39 demonstrates an $IC_{50}$ of about 0.04 nM in the $T_3$ nuclear receptor binding assay. Furthermore, said compound of example 26 significantly lowers serum cholesterol at a daily dose of about 20 micrograms (μg)/kg p.o. in the rat and about 10 μg/kg p.o. in the dog. Furthermore, Lp(a) levels in the normolipemic cynomolgus monkeys are lowered by about 40% after 4 week treatment with the said compound of example 26 at a daily oral dose of 75 μg/kg.

The following Examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1

N-{4-[3-(2,2-Dimethylpropylsulfamoyl)-4-hydroxyphenoxy]-3,5-dimethylphenyl}oxamic acid

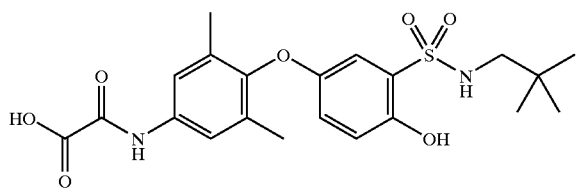

A. 3,5-Dimethyl-4-(4'-methoxyphenoxy)nitrobenzene

A suspension of sodium hydride (NaH; 60% dispersion in mineral oil; 64.11 g, 1.603 mol) in 350 mL of N-methylpyrrolidone (NMP) is cooled to 0° C. and treated with a solution of 4-methoxyphenol (208.4 g, 1.679 mol) over 30 min. The mixture is warmed to room temperature (RT) and after 30 min, 4-chloro-3,5-dimethylnitrobenzene (283.2 g, 1.526 mol; prepared by the method described by Yokoyama et. al. in EP580550) is added in one portion and the reaction is heated at 120° C. for 2 h. The reaction is cooled to room temperature (RT) and quenched with water (1500 mL). The suspension is cooled to 0° C., stirred for 30 min, then filtered and the filtercake is washed with water and dried in vacuo. The crude product, ethyl acetate (EtOAc; 2100 mL) and charcoal (42.6 g) were heated to reflux and the solids were removed by filtration through celite while hot. The filtrate is concentrated under reduced pressure to ca. 800 mL and the resulting suspension is cooled to 0° C. and stirred for 30 min. The product is collected by vacuum filtration, washed with cold EtOAc and dried in vacuo to afford 3,5-dimethyl-4-(4'-methoxyphenoxy)nitrobenzene: NMR (CDCl$_3$) 2.22 (s, 6H), 3.78 (s, 3H), 6.68 (d, 2H, J=8.7), 6.82 (d, 2H, J=8.7), 8.02 (s, 2H).

B. 3,5-Dimethyl-4-(4'-hydroxyphenoxy)nitrobenzene

A mixture of the title A compound, 3,5-dimethyl-4-(4'-methoxyphenoxy)nitrobenzene (16.4 g, 60 mmol), acetic acid (AcOH; 100 mL) and aqueous 48% hydrobromic acid (HBr; 100 mL) is heated at 120° C. for 16 h. The mixture is cooled to RT, diluted with water (200 mL) and the precipitated product is collected by vacuum filtration, washed with water and hexanes and dried in vacuo to afford 3,5-dimethyl-4-(4'-hydroxyphenoxy)nitrobenzene: NMR (CDCl$_3$) 2.22 (s, 6H), 6.62 (d, 2H, J=8.7), 6.77 (d, 2H, J=8.7), 8.0 (s, 2H).

C. 5-(2,6-Dimethyl-4-nitrophenoxy)-2-hydroxybenzenesulfonic acid

A solution of the title B compound, 3,5-dimethyl-4-(4'-hydroxyphenoxy)nitrobenzene (7.86 g, 30.35 mmol) in 150 mL of dichloromethane (CH$_2$Cl$_2$) is treated with chlorosulfonic acid (2.4 mL, 36.42 mmol) at RT. After 16 h, the reaction mixture is concentrated and the residue is dissolved in small amount of CH$_2$Cl$_2$ (ca. 5 mL). The product is precipitated by addition of brine (100 mL), collected by vacuum filtration, washed with water, hexanes and diethyl ether (Et$_2$O) and dried in vacuo to give 5-(2,6-dimethyl-4-nitrophenoxy)-2-hydroxy-benzenesulfonic acid: NMR (DMSO-d$_6$) 2.18 (s, 6H), 6.67–6.83 (m, 3H), 8.1 (s, 2H), 10.07 (s, 1H).

D. 2-Benzyloxy-5-(2,6-dimethyl-4-nitrophenoxy)benzenesulfonic acid, cesium salt

A solution of the title C compound, 5-(2,6-dimethyl-4-nitrophenoxy)-2-hydroxy-benzenesulfonic acid (6.78 g, 20 mmol) in 100 mL of tetrahydrofuran (THF) and 50 mL of N,N-dimethylformamide (DMF) is treated with cesium carbonate (15.6 g, 48 mmol) and benzyl bromide (7.1 mL, 60 mmol) at RT, then heated at 75° C. for 48 h. The reaction mixture is cooled to RT and quenched with aqueous 1N hydrochloric acid (HCl; 100 mL), and THF is evaporated. The precipitated product is collected by vacuum filtration, washed with water, Et$_2$O, EtOAc and CH$_2$Cl$_2$ and dried to afford 2-benzyloxy-5-(2,6-dimethyl-4-nitrophenoxy) benzenesulfonic acid, cesium salt: NMR (DMSO-d$_6$) 2.18 (s, 6H), 5.10 (s, 2H), 6.74 (dd, 1H, J=8.7, 3.8), 6.97 (d, 1H, J=8.7), 7.11 (d, 1H, J=3.8), 7.23–7.39 (m, 3H), 7.59 (d, 2H, J=7.5), 8.12 (s, 2H).

E. 2-Benzyloxy-(2,6-dimethyl-4-nitrophenoxy)benzenesulfonyl chloride

A suspension of the title D compound, 2-benzyloxy-5-(2, 6-dimethyl-4-nitrophenoxy)benzenesulfonic acid, cesium salt (9.9 9, 20 mmol) in 200 mL of CH$_2$Cl$_2$ is treated with DMF (3.1 mL, 40 mmol), then oxalyl chloride (3.5 mL, 40 mmol) is added over 30 min at RT. The reaction mixture is stirred for 1 h further, then diluted with Et$_2$O (200 mL) and washed with water and brine, dried over anhydrous sodium sulfate (Na$_2$SO$_4$) and concentrated. The product is washed with Et$_2$O (5 mL) and dried in vacuo to afford 2-benzyloxy-5-(2,6-dimethyl-4-nitrophenoxy)benzenesulfonyl chloride: NMR (CDCl$_3$) 2.24 (s, 6H), 5.31 (s, 2H), 7.02 (dd, 1 H, J=8.7, 3.8), 7.10 (d, 1H, J=8.7), 7.32–7.47 (m, 4H), 7.52 (d, 2H, J=7.5), 8.05 (s, 2H).

F. 2-Benzyloxy-5-(2,6-dimethyl-4-nitrophenoxy)-N-(2,2-dimethylpropyl)benzenesulfonamide A solution of the title E compound, 2-benzyloxy-5-(2,6-dimethyl-4-nitrophenoxy)benzenesulfonyl chloride (1.12 g, 2.5 mmol) in 20 mL of CH$_2$Cl$_2$ is treated sequentially with N-methylmorpholine (NMM; 550 mL, 5 mmol) and neopentylamine (442 mL, 3.75 mmol) at RT. After 6 h, the mixture is partitioned between water and EtOAc, and the organic solution is washed with aqueous 1N HCl and brine, dried over anhydrous Na$_2$SO$_4$ and concentrated to afford 2-benzyloxy-5-(2,6-dimethyl-4-nitrophenoxy)-N-(2,2-dimethylpropyl)benzenesulfonamide: NMR (CDCl$_3$) 0.78 (s, 9H), 2.22 (s, 6H), 2.58 (d, 2H, J=7.5), 4.82 (t, 1H, J=7.5), 5.18 (s, 2H), 6.88 (dd, 1H, J=9, 3.7), 7.03, (d, 1H, J=9), 7.33–7.51 (m, 6H), 8.04 (s, 2H).

G. 5-(4-Amino-2,6-dimethylphenoxy)-2-benzyloxy-N-(2,2-dimethylpropyl)benzenesulfonamide A mixture of the title F compound, 2-benzyloxy-5-(2,6-dimethyl-4-nitrophenoxy)-N-(2,2-dimethylpropyl) benzenesulfonamide (1.22 g, 2.45 mmol) and palladium on activated carbon (10 wt. %; 250 mg) in 40 mL of THF is stirred under hydrogen atmosphere (H₂, 1 atm) for 8 h. The catalyst is removed by vacuum filtration through celite, washed with THF and the combined filtrate and washings are concentrated. The residue is suspended in CH₂Cl₂ and the product is collected by vacuum filtration, washed with CH₂Cl₂ and dried to give 5-(4-amino-2,6-dimethylphenoxy)-2-hydroxy-N-(2,2-dimethylpropyl)benzenesulfonamide: NMR (DMSO-d₆) 0.80 (s, 9H), 1.90 (s, 6H), 2.55 (d, 2H, J=7.5), 4.90 (br s, 2H), 6.31 (s, 2H), 6.87 (br s, 1H), 6.93 (br s, 2H), 6.97 (t, 1H, J=7.5), 10.13 (s, 1H).

H. N-{4-[3-(2,2-Dimethylpropylsulfamoyl)-4-hydroxyphenoxy]-3,5-dimethylphenyl}-oxamic acid A solution of the title G compound, 5-(4-amino-2,6-dimethylphenoxy)-2-hydroxy-N-(2,2-dimethylpropyl)benzenesulfonamide (750 mg, 1.98 mmol) in 10 mL of THF is cooled to 0° C. and treated sequentially with NMM (545 mL, 4.96 mmol) and ethyl oxalyl chloride (442 mL, 3.96 mmol). The reaction is warmed to RT and after 1 h, quenched with water. The mixture is partitioned between water and EtOAc and the organic solution is washed with aqueous 1N HCl and brine, dried over anhydrous Na₂SO₄ and concentrated. The residue is dissolved in 10 mL of THF, then treated with aqueous 1N lithium hydroxide (LiOH; 1.8 mL, 1.8 mmol) at RT. After 1 h, the reaction is quenched with aqueous 1N HCl and the product is taken up in EtOAc, washed with brine, dried over anhydrous Na₂SO₄ and concentrated. The product is triturated with hexanes, then with Et₂O and dried in vacuo to afford of N-{4-[3-(2,2-dimethylpropyl-sulfamoyl)-4-hydroxyphenoxy]-3,5-dimethylphenyl}oxamic acid: NMR(CDCl₃) 0.89 (s, 9H), 2.13 (s, 6H), 2.70 (d, 2H, J=7.5), 5.22 (t, 1H, J=7.5), 6.84 (d, 1H, J=3.7), 7.04 (d, 1H, J=8.7), 7.15 (dd, 1H, J=8.7, 3.7), 7.33 (s, 2H), 8.54 (br s, 1H), 9.18 (s, 1H); IR (KBr) 1759, 1693; ESI-MS 449 [M−1]⁻.

The following additional compounds may be similarly prepared.

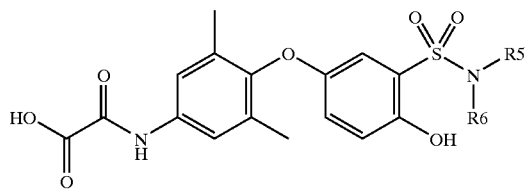

| Example no. R5, R6 | NMR | IR (KBr) | ESI-MS |
|---|---|---|---|
| 2<br>R5 = H, R6 = Ph— | (DMSO-d₆): 1.91 (s, 6H), 6.79–6.99 (m, 6H), 7.11–7.17 (m, 2H), 7.55 (s, 2H), 9.99 (s, 1H), 10.46 (s, 1H), 10.52 (s, 1H) | 1207, 1481, 1689 | 455 [M − 1]⁻ |
| 3<br>R5 = H, R6 = p-FC₆H₄— | (DMSO-d₆): 1.91 (s, 6H), 6.72 (d, 1H, J=3.0), 6.89–7.03 (m, 6H), 7.55 (s, 2H), 9.96 (s, 1H), 10.54 (s, 1H), 10.66 (s, 1H) | 1207, 1481, 1508, 1693 | 473 [M − 1]⁻ |
| 4<br>R5 = H, R6 = o-FC₆H₄— | (MeOH-d₄): 1.98 (s, 6H), 6.81 (d, 1H, J=2.6), 6.87–7.14 (m, 5H), 7.36 (td, 1H, J=7.9, 1.9), 7.46 (s, 2H) | 1209, 1481, 1500, 1689 | 473 [M − 1]⁻ |
| 5<br>R5 = H, R6 = m-FC₆H₄— | (DMSO-d₆): 1.97 (s, 6H), 6.75–6.84 (m, 4H), 6.92 (d, 1H, J=8.8), 7.04 (dd, 1H, J=8.8, 7.20 (app q, 1H, J=7.0), 7.58 (s, 2H), 10.35 (s, 1H), 10.59 (s, 1H), 10.66 (s, 1H) | 1238, 1475, 1706 | 473 [M − 1]⁻ |
| 6<br>R = H, R6 = p-MeOC₆H₄— | (DMSO-d₆): 1.90 (s, 6H), 3.67 (s, 3H), 6.68 (d, 1H, J=3), 6.73 (d, 2H, J=9.00), 6.89–6.99 (m 4H), 7.54 (s, 2H), 9.58 (s, 1H), 10.45 (s, 1H), 10.64 (s, 1H) | 1209, 1475, 1514, 1688 | 485 [M − 1]⁻ |
| 7<br>R5 = H, R6 = p-FC₆H₄CH₂— | (DMSO-d₆): 2.02 (s, 6H), 4.03 (d, 2H, J=6.4), 6.80–6.89 (m, 3H), 7.01, (t, 2H, J=4.0), 7.22 (dd, 2H, J=6.3, 8.7), 7.56 (s, 2H), 7.77 (t, 1H, J=6.4), 10.32 (s, 1H), 10.64 (s, 1H) | 1224, 1481, 1695 | 487 [M − 1]⁻ |
| 8<br>R5 = Me—, R6 = Ph— | (CDCl₃): 1.96 (s, 6H), 3.14 (s, 3H), 6.54 (d, 1H, J=2.4), 6.84–6.85 (m, 2H), 6.88–7.03 (m, 2H), 7.20–7.28 (m, 5H) | 1209, 1230, 1481, 1691 | 469 [M − 1]⁻ |
| 9<br>R5 = H, R6 = n-Pr— | (CDCl₃): 0.87 (t, 3H, J=7.5), 1.38–1.56 (m, 2H), 2.11 (s, 6H), 2.94 (app q, 2H, J=7.5), 5.0 (t, 1H, J=7.5), 6.84 (d, 1H, J=3), 7.0 (d, 1H, J=9), 7.08 (dd, 1H, J=9, 3), 7.32 (s, 2H), 8.44 (br s, 1H), 9.0 (br s, 1H) | 1214, 1485, 1693, 1751 | 421 [M − 1]⁻<br>440 [M + NH₄]⁺ |
| 10<br>R5 = H, R6 = i-Pr— | (DMSO-d₆): 0.95 (d, 6H, J=7.5), 2.02 (s, 6H), 3.2–3.31 (m, 1H), 6.86 (br s, 1H), 6.97 (br s, 2H), 7.06 (d, 1H, J=7.5), 7.57 (s, 2H), 10.32 (brs, 1H), 10.64 (brs, 1H) | 1209, 1485, 1698, 1742 | 421 [M − 1]⁻ |
| 11<br>R5 = H, R6 = n-Bu— | (DMSO-d₆): 0.72 (t, 3H, J=7.5), 1.1–1.35 (m, 4H), 2.03 (s, 6H), 2.76 (app q, 2H, J=7.5), 6.87 (br s, 1H), 6.97 (br s, 2H), 7.1 (t, 1H, J=7.5), 7.58 (s, 2H) | 1321, 1481, 1691 | 435 [M − 1]⁻<br>454 [M + NH₄]⁺ |
| 12<br>R5 = H, R6 = i-Bu— | (DMSO-d₆): 0.75 (d, 6H, J=8.2), 1.49–1.62 (m 1H), 2.03 (s, 6H), 2.55 (app t, 2H, J=6.8), 6.85 (br s, 1H), 6.96 (br s, 2H), 7.17 (t, 1H, J= 6.8), 7.57 (s, 2H), 10.25 (br s, 1H), 10.61 (br s, 1H) | 1209, 1481, 1693, 1762 | 435 [M − 1]⁻ |

-continued

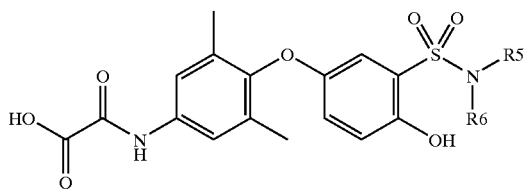

| Example no. R5, R6 | NMR | IR (KBr) | ESI-MS |
|---|---|---|---|
| 13<br>R5 = H, R6 = t-Bu— | (DMSO-$d_6$): 1.02 (s, 9H), 2.03 (s, 6H), 6.81–7.02 (m, 4H), 7.56 (s, 2H), 10.20 (br s, 1H), 10.61 (brs, 1H) | 1204, 1486, 1645, 1754 | 435 [M − 1]$^-$ |
| 14<br>R5 = H, R6 = Cyclohexyl | (CDCl$_3$): 1.06–1.32 (m, 5H), 1.5–-1.73 (m, 5H) 2.01 (s, 6H), 3.02–3.14 (m, 1H), 5.05 (d, 1H, J=7.5), 6.82 (d, 1H, J=3), 6.97 (d, 1H, J=9), 7.10 (dd, 1H, J=9, 3), 7.32 (s, 2H), 8.52 (br s, 1H), 9.06 (brs, 1H) | 1209, 1481, 1695, 1741 | 461 [M − 1]$^-$ |
| 15<br>R5 = Me—, R6 = Me— | (MeOH-$d_4$): 2.07 (s, 6H), 2.64 (s, 6H), 6.86–6.94 (m, 3H), 7.39 (s, 2H) | 1234, 1486, 1685 | 407 [M − 1]$^-$ |
| 16<br>R5, R6 = —(CH$_2$)$_4$— | (MeOH-$d_4$): 1.76–1.80 (m, 4H), 2.08 (s, 6H), 3.21–3.29 (m, 4H), 6.88–6.95 (m, 3H), 7.40 (s, 2H) | 1230, 1479, 1693 | 433 [M − 1]$^-$ |
| 17<br>R5, R6 = —(CH$_2$)$_5$— | (MeOH-$d_4$): 1.49–1.58 (m, 6H), 2.13 (s, 6H), 3.08–3.10 (m, 4H), 6.92–7.02 (m, 3H), 7.53 (s, 2H) | 1207, 1481, 1658 | 447 [M − 1]$^-$ |
| 18<br>R5 = H, R6 = MeOCH$_2$CH$_2$— | (CDCl$_3$): 2.06 (s, 6H), 3.03 (t, 2H, J=5.5), 3.2 (s, 3H), 3.35 (t, 2H, J=5.5), 6.85 (br s, 2H), 6.97 (br s, 1H), 7.34 (s, 2H) | 1218, 1483, 1689 | 437 [M − 1]$^-$ |
| 19<br>R5, R6 = —(CH$_2$)$_2$O(CH$_2$)$_2$— | (MeOH-$d_4$): 2.13 (s, 6H), 3.12 (t, 4H, J=6), 3.68 (t, 4H, J=6), 6.95–7.03 (m, 3H), 7.54 (s, 2H) | 1479, 1711, 1745 | 449 [M − 1]$^-$ |
| 20<br>R5, R6 = —(CH$_2$)$_2$SO$_2$(CH$_2$)$_2$— | (CDCl$_3$): 2.12 (s,6H), 3.10–3.13 (m, 4H), 3.74–3.76 (m, 4H), 6.92–6.99 (m, 3H), 7.41 (s, 2H) | 1209, 1481, 1697 | 497 [M − 1]$^-$ |
| 21<br>R5 = H, R6 = 3-Pyridyl | (DMSO-$d_6$): 1.95 (s, 6H), 6.81 (d, 1H, J=3), 6.92 (d, 1H, J=9), 7.00 (dd, 1H, J=9, 3), 7.26 (dd, 1H, J=8, 5), 7.41–7.45 (m, 1H), 7.56 (s, 2H), 8.21 (dd, 1H, J=5, 1.5), 8.27 (d, 1H, J=2.5), 10.34 (s, 1H), 10.66 (s, 1H) | 1481, 1500, 1689 | 473 [M − 1]$^-$ |
| 22<br>R5 = H,<br>R6 = 5-(1-methyl-2-oxo-1,2-dihydropyridinyl) | (DMSO-$d_6$): 1.88 (s, 6H), 3.75 (s, 3H), 6.64–6.69 (m, 2H), 6.93 (d, 1H, J=9), 6.99 (dd, 1H, J=9, 2.5), 7.32 (dd, 1H, J =9, 2.5), 7.53 (s, 2H), 7.77 (d, 1H, J=2.5), 9.74 (s, 1H), 10.56 (s, 1H), 10.61 (s, 1H) | | 488 [M − 1]$^+$ |

EXAMPLE 23

N-{4-[3-(4-Fluorophenylsulfamoyl)-4-hydroxyphenylsulfanyl]-3,5-dimethylphenyl}oxamic acid

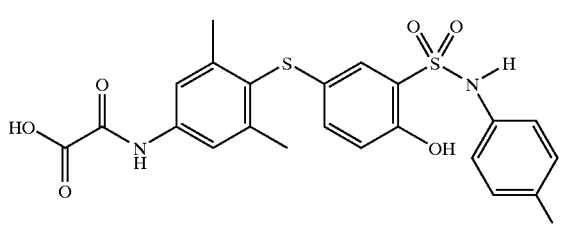

The title compound is prepared similarly to Example 1: NMR (DMSO-$d_6$) 2.21 (s, 6H), 6.87 (d, 1H, J=8.3), 6.95–7.12 (m, 6H), 7.65 (s, 2H), 9.99 (s, 1H), 10.73 (s, 1H), 10.97 (s, 1H); IR (KBr) 1163, 1506, 1690; ESI-MS 489 [M−1]$^-$, 508 [M+NH$_4$]$^+$.

EXAMPLE 24

N-{4-[3-(4-Fluorophenylsulfamoyl)phenoxy]-3,5-dimethylphenyl}oxamic acid

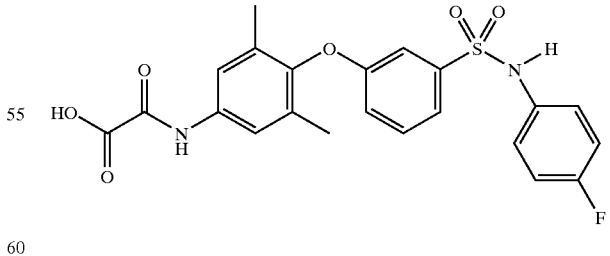

The title compound is similarly to Example 1: NMR (DMSO-$d_6$) 1.91 (s, 6H), 6.73–6.74 (m, 1H), 6.95–7.00 (m, 2H), 7.04–7.10 (m, 2H), 7.21 (dd, 1H, J=8.2, 2.4), 7.35 (d, 1H, J=8.0), 7.52 (app t, 1H, J=8.0), 7.59 (s, 2H), 10.21 (s, 1H), 10.75 (s, 1H); IR (KBr) 1161, 1223, 1509, 1697; ESI-MS 457 [M−1]$^-$, 476 [M+NH$_4$]$^+$.

EXAMPLE 25

N-{4-[3-(4-Fluorophenylsulfamoyl)-4-hydroxyphenoxy]-3-methylphenyl}oxamic acid

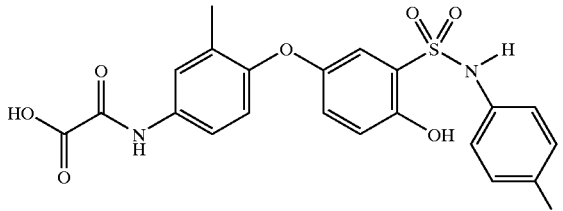

The title compound is prepared similarly to Example 1: NMR (DMSO-$d_6$) 2.06 (s, 3H), 6.65 (d, 1H, J=8.8), 6.92–7.18 (m, 7H), 7.55 (m, 7H), 7.55 (dd, 1H, J=8.8, 2.4), 7.70 (d, 1H, J=2.4), 9.98 (s, 1H), 10.69 (s, 1H), 10.72 (s, 1H), 10.75 (s, 1H); IR (KBr) 1326, 1487, 1506, 1692; ESI-MS 457 [M−1]$^-$.

EXAMPLE 26

N-{4-[3-(4-Fluorobenzenesulfonyl)-4-hydroxyphenoxy]-3,5-dimethylphenyl}oxamic acid

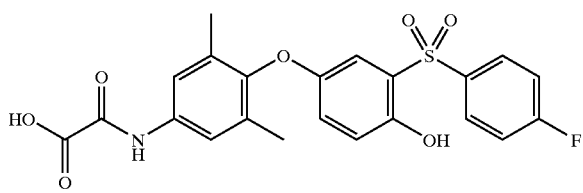

A. 4-Fluorobenzenesulfinic acid

A solution of 4-fluorobenzenesulfonyl chloride (2 g, 10.28 mmol) in 50 mL of THF (distilled from Na-benzophenone) is cooled to 0+ C. and sodium borohydride (1.9 g, 51.4 mmol) is added portionwise. The reaction is stirred at 0° C. for 2 h, then warmed to RT, and after 2 h, quenched with water (5 mL). The solvent is evaporated and the aqueous residue is acidified by addition of aqueous 6N HCl. The product is taken up in EtOAc, washed with brine, dried over anhydrous Na$_2$SO$_4$ and concentrated to give 4-fluorobenzenesulfinic acid: NMR (DMSO-$d_6$) 7.12 (app t, 2H, J=8.3), 7.5 (dd, 2H, J=8.3, 6); ESI-MS 159 [M−1]$^-$.

B. 2-(4-Fluorobenzenesulfonyl)benzene-1,4-diol

A solution of the title A compound, 4-fluorobenzenesulfinic acid (3 g, 18.75 mmol) in 10 mL of water is added to a solution of 1,4 benzoquinone (1.93 g, 17.86 mmol) in 30 mL of CH$_2$Cl$_2$ at RT. After 4 h, the precipitated product is collected by vacuum filtration and washed with cold CH$_2$Cl$_2$ and dried under vacuum to afford 2-(4-fluorobenzenesulfonyl)-benzene-1,4-diol: NMR (DMSO-$d_6$) 6.73 (d, 1H, J=9), 6.92 (dd, 1H, J=9, 3), 7.31 (d, 1H, J=3), 7.41 (app t, 2H, J=9), 7.96 (dd, 2H, J=9, 5), 9.41 (s, 1H), 10.05 (s, 1H); ESI-MS 267 [M−1]$^{-1}$.

C. 4-(2,6-Dimethyl-4-nitrophenoxy)-2-(4-fluorobenzenesulfonyl)phenol

The title B compound, 2-(4-fluorobenzenesulfonyl)benzene-1,4-diol (1.2 g, 4.48 mmol) is added to a suspension of NaH (60% dispersion in mineral oil; 0.39 g, 9.86 mmol) in 15 mL of NMP at 0° C. in one portion. The mixture is warmed to RT and after 30 min, 4-chloro-3,5-dimethylnitrobenzene (1 g, 5.38 mmol) is added and the reaction is heated at 120° C. for 1 h. The reaction is cooled to RT and quenched with aqueous 1N HCl. The mixture is partitioned between water and EtOAc, and the organic solution is washed with water and brine, dried over anhydrous Na$_2$SO$_4$ and concentrated. Chromatography on silica (eluant; EtOAc/hexane-1/2/1/1) affords 4-(2,6-dimethyl-4-nitrophenoxy)-2-(4-fluorobenzenesulfonyl)phenol: NMR (CDCl$_3$) 2.11 (s, 6H), 6.85–6.96 (m, 3H), 7.00 (app t, 2H, J=9), 7.88 (dd, 2H, J=9, 5), 7.98 (s, 2H), 8.73 (s, 1H).

D. 4-(4-Amino-2,6-dimethylphenoxy)-2-(4-fluorobenzenesulfonyl)phenol

A mixture of the title C compound, 4-(2,6-dimethyl-4-nitrophenoxy)-2-(4-fluorobenzenesulfonyl)phenol (0.69 g, 1.65 mmol) and palladium on activated carbon (10 wt. %; 69 mg) in 10 mL of EtOH and 10 mL of CH$_2$Cl$_2$ is stirred under hydrogen atmosphere (H$_2$, 1 atm) for 6 h. The catalyst is removed by vacuum filtration through celite, washed with a 1/1-mixture of EtOH and CH$_2$Cl$_2$, and the combined filtrate and washings are concentrated and dried under vacuum to give 4-(4-amino-2,6-dimethylphenoxy)-2-(4-fluorobenzenesulfonyl)phenol: NMR (DMSO-$d_6$) 1.93 (s, 6H), 4.92 (s, 2H), 6.34 (s, 2H), 6.85 (d, 1 H, J=9), 7.00 (dd, 1 H, J=9, 3), 7.12 (d, 1H, J=3), 7.43 (app t, 2H, J=9), 7.94 (dd, 2H, J=9, 5), 9.41 (s, 1H), 10.4 (s, 1H).

E. N-{4-[3-(4-Fluorobenzenesulfonyl)-4-hydroxyphenoxy]-3,5-dimethylphenyl}oxamic acid ethyl ester A mixture of the title D compound, 4-(4-amino-2,6-dimethylphenoxy)-2-(4-fluorobenzenesulfonyl)phenol (0.64 g, 1.65 mmol) and 2 mL of diethyl oxalate is heated at 180° C. for 3 h. The reaction is cooled to RT and diethyl oxalate is removed under vacuum. Chromatography on silica (eluant; EtOAc/hexane-1/3?2/3) affords N-{4-[3-(4-fluorobenzenesulfonyl)-4-hydroxyphenoxy]-3,5-dimethylphenyl}oxamic acid ethyl ester: NMR (CDCl$_3$) 1.46 (t, 3H, J=7.5), 2.06 (s, 6H), 4.42 (q, 2H, J=7.5), 6.90–6.98 (m, 3H), 7.22 (app t, 2H, J=8.3), 7.40 (s, 2H), 7.87–7.93 (m, 2H), 8.87 (br s, 1H); ESI-MS 486 [M−1]$^-$.

F. N-{4-[3-(4-Fluorobenzenesulfonyl)-4-hydroxyphenoxy]-3,5-dimethylphenyl}oxamic acid A solution of the title E compound, N-{4-[3-(4-fluorobenzenesulfonyl)-4-hydroxyphenoxy]-3,5-dimethylphenyl}oxamic acid ethyl ester (773 mg, 1.58 mmol) in 15 mL of EtOH is treated with aqueous 1N sodium hydroxide (NaOH; 4.75 mL, 4.75 mmol) at RT. After 1 h, the reaction is quenched with aqueous 1N HCl (5.5 mL) and the product is taken up in EtOAc, washed with brine, dried over anhydrous Na$_2$SO$_4$ and concentrated. The product is triturated with Et$_2$O and dried in vacuo to afford N-{4-[3-(4-fluorobenzenesulfonyl)-4-hydroxyphenoxy]-3,5-dimethylphenyl}oxamic acid: NMR (DMSO-$d_6$) 2.06 (s, 6H), 6.88 (d, 1H, J=9), 7.03 (dd, 1H, J=9,3), 7.13 (d, 1H, J=3), 7.43 (app t, 2H, J=9), 7.61 (s, 2H), 7.94 (dd, 2H, J=9,5), 10.5 (s, 1H), 10.69 (s, 1H); IR (KBr) 1240, 1481, 1685, 1764; ESI-MS 458 [M−1]$^-$.

The following additional compounds are similarly prepared.

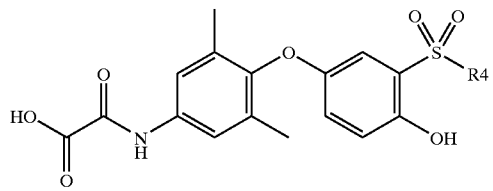

| Example R4 | NMR | IR (KBr) | ESI-MS |
| --- | --- | --- | --- |
| 27<br>R4 = Ph— | (MeOH-d$_6$): 2.02 (s, 6H), 6.85 (d, 1H, J=7), 6.98 (dd, 1H, J=7, 2.3), 7.26 (d, 1H, J=2.3), 7.53 (s, 2H), 7.55–7.68 (m, 3H), 7.93 (d, 2H, J=7) | 1209, 1479, 1697 | 440 [M − 1]$^-$ |
| 28<br>R4 = p-ClC$_6$H$_4$— | (MeOH-d$_6$): 2.12 (s, 6H), 6.84 (d, 1H, J=8.3), 6.96 (dd, 1H, J=8.3, 3), 7.24 (d, 1H, J=3), 7.53 (d, 2H, J=7.5), 7.58 (s, 2H), 7.90 (d, 2H, J=7.5) | 1207, 1479, 1697 | 474 [M − 1]$^-$ |
| 29<br>R4 = p-MeC$_6$H$_4$— | (MeOH-d$_6$): 2.10 (s, 6H), 2.41 (s, 3H), 6.82 (d, 1H, J=9), 6.95 (dd, 1H, J=9, 3), 7.19 (d, 1H, J=3), 7.45 (d, 2H, J=8.3), 7.53 (s, 2H), 7.77 (d, 2H, J=8.3) | 1149, 1207, 1481 | 454 [M − 1]$^+$<br>473 [M + NH$_4$]$^+$ |
| 30<br>R4 = p-MeOC$_6$H$_4$— | (CDCl$_3$): 1.98 (s, 6H), 3.80 (s, 3H), 6.80–6.82 (m, 2H), 6.89–6.93 (m, 3H), 7.31 (s, 2H), 7.73 (d, 2H, J=7.2), 8.73 (br s, 1H), 8.89 (br s, 1H) | 1209, 1475, 1588, 1705 | 470 [M − 1]$^-$ |
| 31<br>R4 = p-CF$_3$C$_6$H$_4$— | (DMSO-d$_6$): 2.07 (s, 6H), 6.89 (d, 1H, J=9), 7.08 (dd, 1H, J=9, 3), 7.15 (d, 1H, J=3), 7.60 (s, 2H), 7.98 (d, 2H, J=3), 8.08 (d, 2H, J=3) | 1207, 1476, 1697 | 508 [M − 1]$^-$ |
| 32<br>R4 = Me— | (MeOH-d$_4$): 2.12 (s, 6H), 3.23 (s, 3H), 6.96–7.0 (m, 2H), 7.11 (d, 1H, J=2.2), 7.51 (s, 2H) | 1205, 1481, 1687, 1739 | 378 [M − 1]$^-$ |
| 33<br>R4 = n-Bu— | (DMSO-d$_6$): 0.81 (t, 3H, J=7.2), 1.24–1.36 (m, 2H), 1.41–1.51 (m, 2H), 2.04 (s, 6H), 3.37 (t, 2H, J=7.2), 6.88 (d, 1H, J=3), 7.08 (dd, 1H, J=9, 3), 7.15 (d, 1H, J=3), 7.00–7.10 (m, 2H), 7.57 (s, 2H), 10.67 (s, 2H) | 1205, 1488, 1694 | 420 [M − 1]$^-$<br>439 [M + NH$_4$]$^+$ |
| 34<br>R4 = i-Pr— | (DMSO-d$_6$): 1.11 (d, 6H, J=7), 2.03 (s, 6H), 3.66–3.75 (m, 1H), 6.88 (d, 1H, J=3), ), 7.02 (d, 1H, J=3), 7.08 (dd, 1H, J=9, 3), 7.57 (s, 2H), 10.65 (s, 2H) | 1229, 1354, 1480, 1688, 1761 | 406 [M − 1]$^-$<br>425 [M + NH$_4$]$^+$ |

EXAMPLE 35

N-{4-[3-(4-Fluorobenzenesulfonyl)-4-hydroxyphenoxy]-3,5-dimethylphenyl}malonamic acid

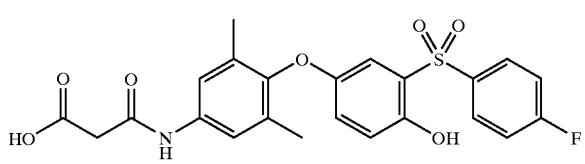

The title compound is prepared similarly to Example 26: NMR (DMSO-d$_6$) 2.05 (s, 6H), 3.35(s, 2H), 6.89 (d, 1H, J=9), 7.01 (dd, 1H, J=9, 3), 7.14 (d, 1H, J=3), 7.39–7.45 (m, 4H,), 7.93 (dd, 2H, J=8.8, 5.2), 10.18 (s, 1H), 10.55 (s, 1H), 12.6 (brs, 1H); IR (KBr) 1142, 1239, 1485, 1623, 1654, 1736; ESI-MS 472 [M−1]$^-$.

EXAMPLE 36

N-{4-[3-(4-Fluorobenzenesulfonyl)-4-hydroxyphenoxy]-3,5-dimethylphenyl}succinamic acid

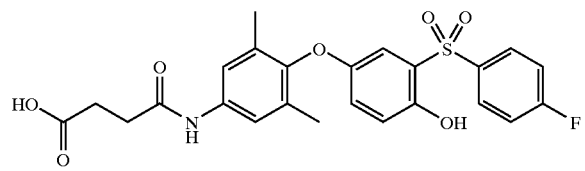

The title compound is prepared similarly to Example 26: NMR-(DMSO-d$_6$) 2.04 (s, 6H), 2.50–2.56 (m, 4H), 6.87 (d, 1H, J=9), 7.01 (dd, 1H, J=9, 3), 7.12 (d, 1H, J=3), 7.39–7.45 (m, 4H), 7.93 (dd, 2H, J=8.8, 5.2), 9.93 (s, 1H), 10.5 (br s, 1H), 12.1 (s, 1H); IR (KBr) 1480, 1659, 1717; ESI-MS 486 [M−1]$^-$.

EXAMPLE 37

3-{4-[3-(4-Fluorobenzenesulfonyl)-4-hydroxyphenoxy]-3,5-dimethylphenylamino}-propionic acid

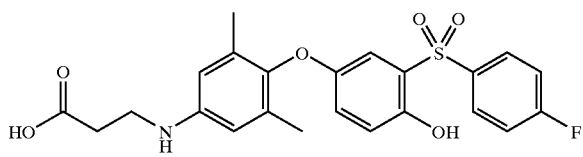

The title compound is prepared similarly to Example 26: NMR (MeOH-d$_4$) 2.06 (s, 6H), 2.65 (t, 2H, J=7), 3.49 (t, 2H, J=7), 6.82 (d, 1H, J=9), 6.85 (s, 2H), 6.94 (dd, 1H, J=9, 3), 7.15 (d, 1H, J=3), 7.23 (app t, 2H, J=9), 7.88–7.93 (m, 2H); IR (KBr) 1199, 1493, 1675; ESI-MS 460 [M+1]$^+$, 458 [M−1]$^-$.

EXAMPLE 38

N-{4-[3-(4-Fluorobenzenesulfonyl)-4-hydroxyphenoxy]-3-methylphenyl}oxamic acid

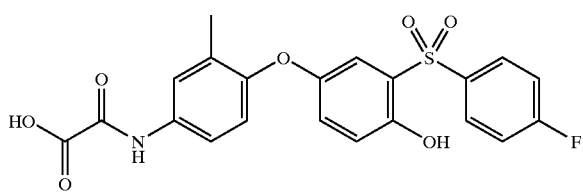

The title compound is prepared similarly to Example 26: NMR (DMSO-d$_6$) 2.18 (s, 3H), 6.90 (d, 1H, J=9), 6.92 (d, 1H, J=9), 7.16 (dd, 1H, J=9,3), 7.34 (d, 1H, J=3), 7.43 (app t, 2H, J=9), 7.61 (dd, 1H, J=9, 3), 7.74 (d, 1H, J=3), 7.97 (dd, 2H, J=9,5), 10.67 (s, 1H), 10.71 (s, 1H); IR (KBr) 1234, 1495, 1697; ESI-MS 444 [M−1]$^-$.

EXAMPLE 39

N-{3,5-Dibromo-4-[3-(4-fluorobenzenesulfonyl)-4-hydroxyphenoxy]phenyl}oxamic acid

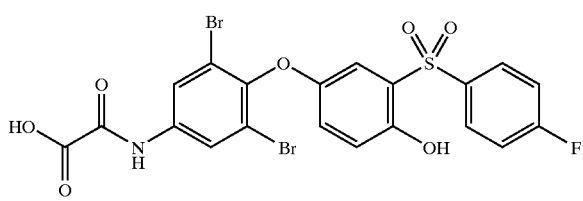

The title compound is prepared analogously to Example 26: NMR (DMSO-d$_6$) 6.91 (d, 1H, J=9), 7.09 (dd, 1H, J=9,3), 7.20 (d, 1 H, J=3), 7.44 (app t, 2H, J=8.6), 7.92–7.97 (m, 2H), 8.27 (s, 2H), 10.74 (s, 1H), 11.15 (s, 1H); IR (KBr) 1290, 1454, 1484, 1589, 1695; ESI-MS 588 [M−1]$^-$.

EXAMPLE 40

N-{4-[3-(4-Fluorobenzenesulfonyl)-4-hydroxyphenoxy]-3,5-dimethylphenyl}oxalamide

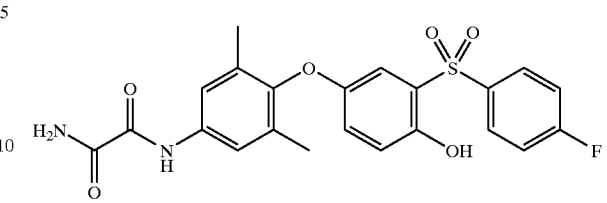

The title compound is prepared analogously to Example 26: NMR (DMSO-d$_6$) 2.06 (s, 6H), 6.88 (d, 1H, J=9), 7.03 (dd, 1H, J=9, 3), 7.13 (d, 1H, J=3), 7.42 (app t, 2H, J=8.9), 7.66 (s, 2H), 7.92–7.96 (m, 2H), 8.0 (br s, 1H), 8.29 (br s, 1H), 10.49 (s, 1H), 10.58 (s, 1H); IR (KBr) 1141, 1250, 1481, 1676; ESI-MS 497 [M−1]$^-$, 475 [M+NH$_4$]$^+$.

EXAMPLE 41

N-{4-[3-(4-Fluorobenzenesulfonyl)-4-hydroxyphenoxy]-3,5-dimethylphenyl}-N'-propyl-oxalamide

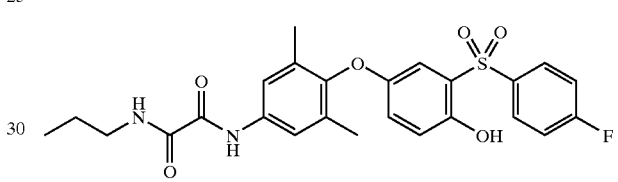

The title compound is prepared analogously to Example 26: ES-MS 499 [M−1]$^-$, 518 [M+NH$_4$]$^+$.

EXAMPLE 42

N-{4-[3-(4-Fluorobenzenesulfonyl)-4-hydroxyphenoxy]-3,5-dimethylphenyl}-N'-isopropyl-oxalamide

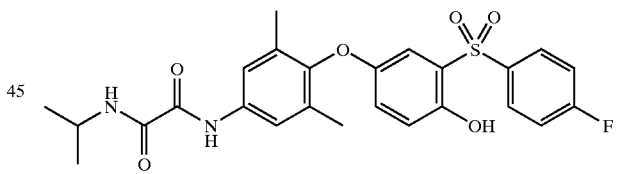

The title compound is prepared analogously to Example 26: ES-MS 499 [M−1]$^-$, 518 [M+NH$_4$]$^+$.

EXAMPLE 43

N-Butyl-N'-{4-[3-(4-fluorobenzenesulfonyl)-4-hydroxyphenoxy]-3,5-dimethylphenyl}-oxalamide

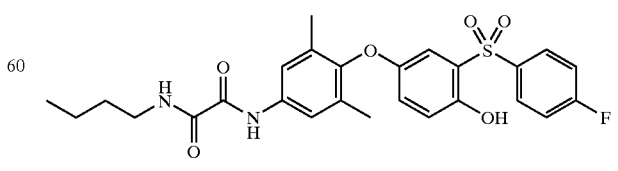

The title compound is prepared analogously to Example 26: ES-MS 513 [M−1]$^-$, 515 [M+1]$^+$, 532 [M+NH$_4$]$^+$.

EXAMPLE 44

N-{4-[3-(4-Fluorobenzenesulfonyl)-4-hydroxyphenoxy]-3,5-dimethylphenyl}-N'-2-methoxyethyl)oxalamide

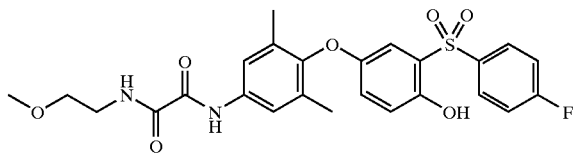

The title compound is prepared analogously to Example 26: ES-MS 517 [M+1]$^+$.

EXAMPLE 45

N-{4-[3-(4-Fluorobenzenesulfonyl)-4-hydroxyphenoxy]-3,5-dimethylphenyl}-2-morpholin-4-yl-2-oxoacetamide

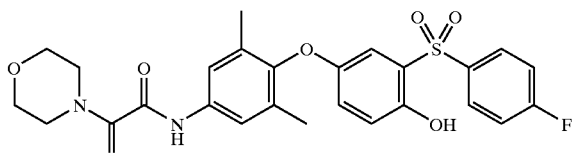

The title compound is prepared analogously to Example 26: ES-MS 527 [M−1]$^-$, 529 [M+1]$^+$, 546 [M+NH$_4$]$^+$.

EXAMPLE 46

N-{4-[4-Hydroxy-3-(piperidine-1-carbonyl)phenoxy]-3,5-dimethylphenyl}oxamic acid

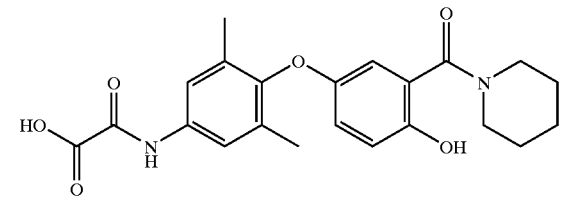

A. 5-(2,6-Dimethyl-4-nitrophenoxy)-2-(2-methoxyethoxymethyl)benzoic acid 2-methoxyethoxymethyl ester A suspension of sodium NaH (60% dispersion in mineral oil; 1.32 g, 33 mmol) in 50 mL of NMP is cooled to 0° C. and 2,5-dihydroxybenzoic acid (1.54 g, 10 mmol) is added in one portion. The mixture is warmed to room temperature, and after 30 min, 4-chloro-3,5-dimethylnitrobenzene (2.41 g, 13 mmol) is added in one portion and the reaction is heated at 120° C. for 3 h. The reaction is cooled to RT and 2-methoxyethoxymethyl chloride (2.85 mL, 25 mmol) is added. After stirring for 30 min, the mixture is poured onto water and the product is taken up in Et$_2$O. The organic solution is washed with brine, dried over anhydrous Na$_2$SO$_4$ and concentrated. Chromatography on silica (eluant; EtOAc/hexane-1/2→3/2) affords 5-(2,6-dimethyl-4-nitrophenoxy)-2-(2-methoxyethoxymethoxy)benzoic acid 2-methoxyethoxymethyl ester: NMR (CDCl$_3$) 2.23 (s, 6H), 3.36 (s, 3H), 3.38 (s, 3H), 3.54–3.60 (m, 4H), 3.80–3.90 (m, 4H), 5.28 (s, 2H), 5.52 (s, 2H), 6.82 (dd, 1H, J=9,3), 7.17–7.23 (m, 2H), 8.02 (s, 2H).

B. 5-(4-Amino-2,6-dimethylphenoxy)-2-(2-methoxyethoxymethoxy)benzoic acid 2-methoxyethoxymethyl ester A mixture of the title A compound, 5-(2,6-dimethyl-4-nitrophenoxy)-2-(2-methoxyethoxymethoxy)benzoic acid 2-methoxyethoxymethyl ester (3.2 g, 6.68 mmol) and palladium on activated carbon (10 wt. %; 320 mg) in 50 mL of EtOAc is stirred under hydrogen atmosphere (H$_2$, 1 atm) for 3 h. The catalyst is removed by vacuum filtration through celite, washed with EtOAc, and the combined filtrate and washings are concentrated and dried under vacuum to give 5-(4-amino-2,6-dimethylphenoxy)-2-(2-methoxyethoxymethoxy)benzoic acid 2-methoxyethoxymethyl ester: NMR (CDCl$_3$) 2.07 (s, 6H), 3.37 (s, 3H), 3.40 (s, 3H), 3.52–3.62 (m, 4H), 3.83–3.92 (m, 4H), 5.26 (s, 2H), 5.52 (s, 2H), 6.60 (s, 2H), 6.80 (dd, 1H, J=8.3, 3), 7.13 (d, 1H, J=8.3), 7.24 (d, 1H, J=3).

C. 5-[4-(Ethoxyoxalylamino)-2,6-dimethylphenoxy]-2-hydroxybenzoic acid

A solution of the title B compound, 5-(4-amino-2,6-dimethylphenoxy)-2-(2-methoxyethoxymethoxy)benzoic acid 2-methoxyethoxymethyl ester (2.83 g, 6.3 mmol) in 20 mL of THF is cooled to 0° C. and treated sequentially with NMM (2.1 mL, 18.9 mmol) and ethyl oxalyl chloride (0.915 mL, 8.19 mmol). After 15 min, the mixture is partitioned between EtOAc and water, and the organic solution is washed with brine, dried over anhydrous Na$_2$SO$_4$ and concentrated. The residue is dissolved in 30 mL of EtOH and 20 mL of aqueous 6N HCl is added. The mixture is stirred at RT for 16 h, and EtOH is removed under reduced pressure. The residue is diluted with water (100 mL), and the solid is collected by vacuum filtration, washed with water and dried. Crystallization from acetonitrile gives 5-[4-(ethoxyoxalylamino)-2,6-dimethylphenoxy]-2-hydroxybenzoic acid: NMR (DMSO-d$_6$) 1.31 (t, 3H, J=7), 2.06 (s, 6H), 4.30 (q, 2H, J=7), 6.88–6.97 (m, 2H), 7.08 (dd, 1H, J=9, 3), 7.54 (s, 2H), 10.7 (s, 1H).

D. N-{4-[4-Hydroxy-3-(piperidine-1-carbonyl)phenoxy]-3,5-dimethylphenyl}oxamic acid A solution of title C compound, 5-[4-(ethoxyoxalylamino)-2,6-dimethylphenoxy]-2-hydroxybenzoic acid (37 mg, 0.1 mmol) in 1 mL of DMF is treated with NMM (55 μL, 0.5 mmol) and 1,1'-carbonyldiimidazole (32 mg, 0.2 mmol) at RT. The reaction mixture is heated at 60° C. for 1 h, then cooled to RT and piperidine (24 μL, 0.24 mmol) is added. After 16 h, the reaction is treated with aqueous 1.5 N LiOH (333 μL, 0.5 mmol). The mixture is agitated for 30 min, and the reaction is quenched with trifluoroacetic acid (TFA; 100 μL). The product is purified by HPLC (mobile phase; acetonitrile-water with 0.1% of trifluoroacetic acid) to afford N-{4-[4-hydroxy-3-(piperidine-1-carbonyl)phenoxy]-3,5-dimethylphenyl}oxamic acid: NMR (DMSO-d$_6$) 1.34–1.63 (m, 6H), 2.06 (s, 6H), 3.30 (br s, 4H), 6.36 (d, 1H, J=2.3), 6.67 (dd, 1H, J=8.3, 2.3), 6.80 (d, 1H, J=8.3), 7.53 (s, 2H), 9.38 (br s, 1H), 10.6 (s, 1H); ESI-MS 413 [M+1]$^+$.

EXAMPLE 47

N-{4-[4-Hydroxy-3-(morpholine-4-carbonyl)phenoxy]-3,5-dimethylphenyl}oxamic acid

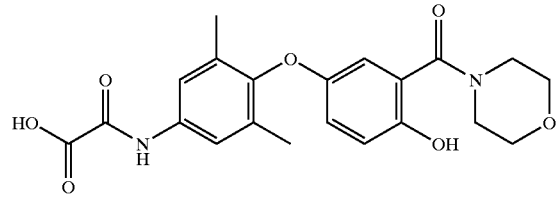

The title compound is prepared similarly to Example 46: ESI-MS 415 [M+1]$^+$.

EXAMPLE 48

N-[4-(3-Cyclohexylcarbamoyl-4-hydroxyphenoxy)-3,5-dimethylphenyl]oxamic acid

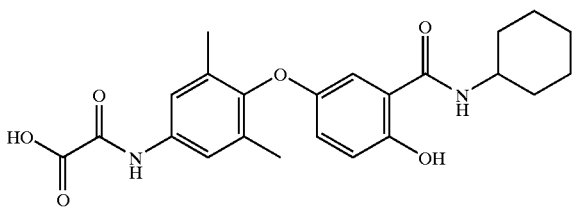

The title compound is prepared similarly to Example 46: ESI-MS 427 [M+1]+.

EXAMPLE 49

N-{4-[4-Hydroxy-3-(2-methoxyethylcarbamoyl) phenoxy]-3,5-dimethylphenyl}oxamic acid

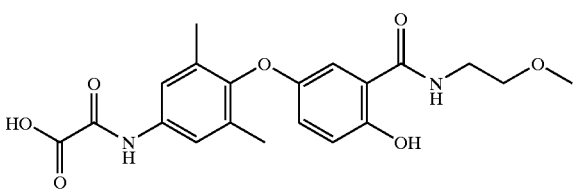

The title compound is prepared similarly to Example 46: ESI-MS 403 [M+1]+.

EXAMPLE 50

N-{4-[4-Hydroxy-3-(2-morpholin-4-yl-ethylcarbamoyl)phenoxy]-3,5-dimethylphenyl}-oxamic acid

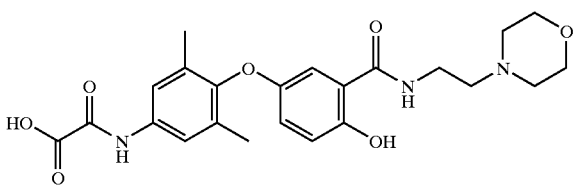

The title compound is prepared similarly to Example 46: ESI-MS 458 [M+1]+.

EXAMPLE 51

N-{4-[4-Hydroxy-3-(pyridin-3-ylcarbamoyl)phenoxy]-3,5-dimethylphenyl}oxamic acid

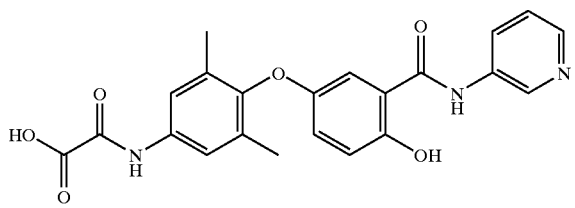

The title compound is prepared similarly to Example 46: ESI-MS 422 [M+1]+.

EXAMPLE 52

Formulation Example: Hard gelatin capsules, comprising 100 mg active substance, for example, N-{4-[3-(4-fluorobenzenesulfonyl)-4-hydroxyphenoxy]-3,5-dimethylphenyl}oxamic acid, can be prepared for example as follows:

| Composition (for 1000 capsules) | |
|---|---|
| Active ingredient | 100.0 g |
| Lactose | 250.0 g |
| Microcrystalline cellulose | 30.0 g |
| Sodium lauryl sulfate | 2.0 g |
| Magnesium stearate | 8.0 g |

The sodium lauryl sulfate is added to the lyophilized active ingredient via a sieve with a mesh size of 0.2 mm. Both components are intimately mixed. Then first the lactose is added via a sieve with a mesh size of 0.6 mm and then the microcrystalline cellulose via a sieve with a mesh size of 0.9 mm. Thereupon these components are intimately mixed for a further 10 minutes. Finally the magnesium stearate is added via a sieve with a mesh size of 0.8 mm. After 3 minutes of further mixing, 390 mg each of the formulation obtained are filled into hard gelatin capsules of size 0.

What is claimed is:

1. A method of lowering Lp(a) levels in mammals which comprises administering to a mammal in need thereof an effective Lp(a) lowering amount of a compound of the formula

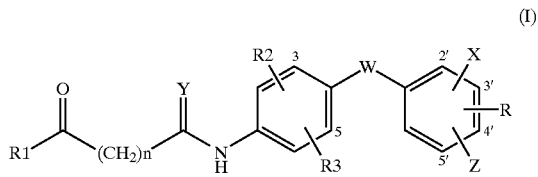

(I)

in which

W is O, S, S(O) or S(O)$_2$;

X is —SR4, —S(O)R4, —S(O)$_2$R4, or —S(O)$_2$NR5R6; or X is —C(O)NR5R6 located at the 3'-, 4'- or 5' position;

Y is O or H$_2$;

Z is hydrogen, halogen, hydroxy, optionally substituted alkoxy, aralkoxy, acyloxy or alkoxycarbonyloxy;

R is hydrogen, halogen, trifluoromethyl, lower alkyl or cycloalkyl;

R1 is hydroxy, optionally substituted alkoxy, aryloxy, heteroaryloxy, aralkoxy, cycloalkoxy, heteroaralkoxy or —NR5R6;

R2 is hydrogen, halogen or alkyl;

R3 is halogen or alkyl;

R4 is optionally substituted alkyl, aryl, aralkyl, heteroaralkyl or heteroaryl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring;

n represents zero or an integer from 1 to 4;

with the proviso that when X is —C(O)NR5R6, Z is different from hydrogen;

or a pharmaceutically acceptable salt thereof.

2. A method according to claim 1 in which W is O and Y is O.

3. A method according to claim 1 of lowering Lp(a) levels in mammals which comprises administering to a mammal in need thereof an effective Lp(a) lowering amount of a compound of formula I in which W is O or S;

X is —S(O)$_2$R4; R4 being lower alkyl, phenyl or phenyl substituted by one or more substituents selected from the group consisting of lower alkyl, lower alkoxy, halogen and trifluoromethyl; or is —S(O)$_2$NR5R6; or is —C(O)NR5R6 located at the 3', 4' or 5'-position; R5, in each case, being hydrogen or lower alkyl and R6, in each case, being hydrogen, lower alkyl, lower alkyl substituted by NR5R6, 3- to 7-membered cycloalkyl, phenyl, phenyl substituted by one or more substituents selected from the group consisting of lower alkyl, lower alkoxy, halogen and trifluoromethyl, pyridyl or N-lower alkyl-2-pyridone; or R5 and R6 combined, in each case, being alkylene or alkylene interrupted by O or S(O)$_2$ which together with the nitrogen atom to which they are attached form a 5- to 7-membered ring;

Y is O or H$_2$;

Z is hydrogen or hydroxy;

R is hydrogen;

R1 is hydroxy, lower alkoxy or NR5R6; R5 being hydrogen or lower alkyl and R6 being hydrogen, or lower alkyl, or R5 and R6 combined being alkylene or alkylene interrupted by O which together with the nitrogen atom to which they are attached form a 5- to 7-membered ring;

R2 is hydrogen, halogen or lower alkyl;

R3 is halogen or lower alkyl; and n represents zero, 1 or 2;

with the proviso that when X is —C(O)NR5R6, Z is different from hydrogen;

or a pharmaceutically acceptable salt thereof.

4. A method according to claim 3 in which W is O and Y is O.

5. A method according to claim 1 which comprises administering to a mammal in need thereof of effective Lp(a) lowering amount of a compound of the formula

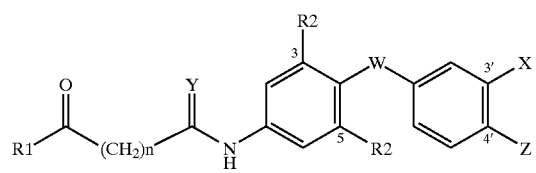

(IA)

in which

W is O or S;

X is —SR4, —S(O)R4, —S(O)$_2$R4, —S(O)$_2$NR5R6 or —C(O)NR5R6;

Y is O or H$_2$;

Z is hydrogen, halogen, hydroxy, alkoxy, aralkoxy, acyloxy or alkoxycarbonyloxy;

R1 is hydroxy, lower alkoxy or aryloxy;

R2 is hydrogen, halogen or lower alkyl;

R3 is halogen or lower alkyl;

R4 is optionally substituted alkyl, aryl, aralkyl, heteroaryl or heteroaralkyl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)$_2$ or NR7 which together with the nitrogen atom to which they are attached form a 5- to 7-membered ring;

n represents zero, 1 or 2;

with the proviso that when X is —C(O)NR5R6, Z is different from hydrogen;

or a pharmaceutically acceptable salt thereof.

6. A method according to claim 5 in which W is O and Y is O.

7. A method according to claim 1 which comprises administering to a mammal in need thereof an effective Lp(a) lowering amount of a compound of the formula

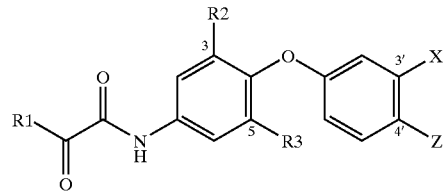

(IB)

wherein

X is —S(O)$_2$R4, —S(O)$_2$NR5R6 or —C(O)NR5R6;

Z is hydroxy, lower alkanoyloxy or alkoxy;

R1 is hydroxy or lower alkoxy;

R2 and R3 are lower alkyl;

R4 is aryl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)2 or NR7 which together with the nitrogen atom to which they are attached form a 5- to 7-membered ring;

or a pharmaceutically acceptable salt thereof.

8. A method according to claim 7 wherein X is —S(O)$_2$R4 or —S(O)$_2$NR5R6.

9. A method of lowering Lp(a) levels in mammals which comprises administering to a mammal in need thereof an effective Lp(a) lowering amount of a compound of the formula

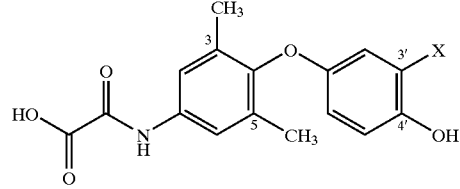

(IC)

wherein

X is —S(O)$_2$R4 or —S(O)$_2$NR5R6;

R4 is monocyclic aryl;

R5, R6 and R7 are independently hydrogen, optionally substituted alkyl or aryl; or R5 and R6 combined are CH$_2$CH$_2$—Q—CH$_2$CH$_2$ wherein Q is CH$_2$, O, NR7, S, S(O) or S(O)$_2$ which together with the nitrogen atom to which they are attached from a 6-membered ring; or a pharmaceutically acceptable prodrug ester thereof; or a pharmaceutically acceptable salt thereof.

10. A method according to claim 9 wherein X is S(O)₂R4 and R4 is phenyl optionally substituted by lower alkyl, halo, lower alkoxy or trifluoromethyl; or a pharmaceutically acceptable salt thereof; or a pharmaceutically acceptable prodrug ester thereof.

11. A method according to claim 10 of lowering Lp(a) levels in mammals which comprises administering to a mammal in need thereof an effective Lp(a) lowering amount of N-{4[3-(4-fluorobenzenesulfonyl)-4-hydroxyphenoxy]-3,5-dimethylphenyl}oxamic acid;

or a pharmaceutically acceptable salt thereof; or a pharmaceutically acceptable prodrug ester thereof.

12. A method of treating cardiovascular conditions in which Lp(a) is implicated which comprises administering to a mammal in need thereof an effective Lp(a) lowering amount of a compound of the formula

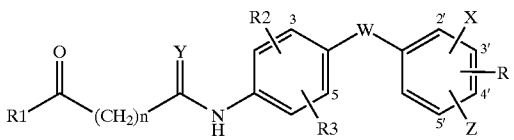

(I)

in which

W is O, S, S(O) or S(O)₂;

X is —SR4, —S(O)R4, —S(O)₂R4, or —S(O)₂NR5R6; or X is —C(O)NR5R6 located at the 3'-, 4'- or 5' position;

Y is O or H₂;

Z is hydrogen, halogen, hydroxy, optionally substituted alkoxy, aralkoxy, acyloxy or alkoxycarbonyloxy;

R is hydrogen, halogen, trifluoromethyl, lower alkyl or cycloalkyl;

R1 is hydroxy, optionally substituted alkoxy, aryloxy, heteroaryloxy, aralkoxy, cycloalkoxy, heteroaralkoxy or —NR5R6;

R2 is hydrogen, halogen or alkyl;

R3 is halogen or alkyl;

R4 is optionally substituted alkyl, aryl, aralkyl, heteroaralkyl or heteroaryl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)₂ or NR7 which together with the nitrogen atom to which they are attached form a 5- to 7-membered ring;

n represents zero or an integer from 1 to 4;

with the proviso that when X is —C(O)NR5R6, Z is different from hydrogen;

or a pharmaceutically acceptable salt thereof.

13. A method according to claim 12 in which W is O and Y is O.

14. A method according to claim 12 in which the compound is a compound of formula I in which W is O or S;

X is —S(O)₂R4; R4 being lower alkyl, phenyl or phenyl substituted by one or more substituents selected from the group consisting of lower alkyl, lower alkoxy, halogen and trifluoromethyl; or is —S(O)₂NR5R6; or is —C(O)NR5R6 located at the 3', 4' or 5'-position; R5, in each case, being hydrogen or lower alkyl and R6, in each case, being hydrogen, lower alkyl, lower alkyl substituted by NR5R6, 3- to 7-membered cycloalkyl, phenyl, phenyl substituted by one or more substituents selected from the group consisting of lower alkyl, lower alkoxy, halogen and trifluoromethyl, pyridyl or N-lower alkyl-2-pyridone; or R5 and R6 combined, in each case, being alkylene or alkylene interrupted by O or S(O)₂ which together with the nitrogen atom to which they are attached form a 5- to 7-membered ring;

Y is O or H₂;

Z is hydrogen or hydroxy;

R is hydrogen;

R1 is hydroxy, lower alkoxy or NR5R6; R5 being hydrogen or lower alkyl and R6 being hydrogen or lower alkyl, or R5 and R6 combined being alkylene or alkylene interrupted by O which together with the nitrogen atom to which they are attached form a 5- to 7-membered ring;

R2 is hydrogen, halogen or lower alkyl;

R3 is halogen or lower alkyl; and n represents zero, 1 or 2;

with the proviso that when X is —C(O)NR5R6, Z is different from hydrogen;

or a pharmaceutically acceptable salt thereof.

15. A method according to claim 14 in which W is O and Y is O.

16. A method according to claim 12 in which the compound is a compound of the formula

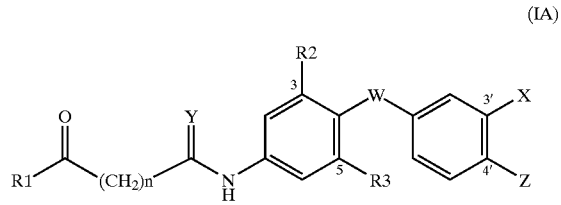

(IA)

in which

W is O or S;

X is —SR4, —S(O)R4, —S(O)₂R4, —S(O)₂NR5R6 or —C(O)NR5R6;

Y is O or H₂;

Z is hydrogen, halogen, hydroxy, alkoxy, aralkoxy, acyloxy or alkoxycarbonyloxy;

R1 is hydroxy, lower alkoxy or aryloxy;

R2 is hydrogen, halogen or lower alkyl;

R3 is halogen or lower alkyl;

R4 is optionally substituted alkyl, aryl, aralkyl, heteroaryl or heteroaralkyl;

R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)₂ or NR7 which together with the nitrogen atom to which they are attached form a 5- to 7-membered ring;

n represents zero, 1 or 2;

with the proviso that when X is —C(O)NR5R6, Z is different from hydrogen;

or a pharmaceutically acceptable salt thereof.

17. A method according to claim 16 in which W is O and Y is O.

18. A method according to claim 12 in which the compound is a compound of the formula

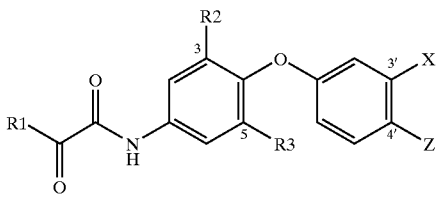

(IB)

wherein
X is —S(O)₂R4, —S(O)₂NR5R6 or —C(O)NR5R6;
Z is hydroxy, lower alkanoyloxy or alkoxy;
R1 is hydroxy or lower alkoxy;
R2 and R3 are lower alkyl;
R4 is aryl;
R5, R6 and R7 are independently hydrogen, optionally substituted alkyl, cycloalkyl, aryl, aralkyl, heteroaryl, or heteroaralkyl; or R5 and R6 combined are alkylene optionally interrupted by O, S, S(O), S(O)₂ or NR7 which together with the nitrogen atom to which they are attached form a 5- to 7-membered ring;
or a pharmaceutically acceptable salt thereof.

19. A method according to claim 18 wherein X is —S(O)₂R4 or —S(O)₂NR5R6.

20. A method of treating cardiovascular conditions in which Lp(a) is implicated which comprises administering to a mammal in need thereof an effective Lp(a) lowering amount of a compound of the formula

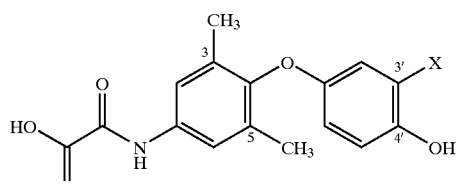

(IC)

wherein
X is —S(O)₂R4 or —S(O)₂NR5R6;
R4 is monocyclic aryl;
R5, R6 and R7 are independently hydrogen, optionally substituted alkyl or aryl; or R5 and R6 combined are CH₂CH₂—Q—CH₂CH₂ wherein Q is CH₂, O, NR7, S, S(O) or S(O)₂ which together with the nitrogen atom to which they are attached from a 6-membered ring; or a pharmaceutically acceptable prodrug ester thereof; or a pharmaceutically acceptable salt thereof.

21. A method according to claim 12 wherein X is S(O)₂R4 and R4 is phenyl optionally substituted by lower alkyl, halo, lower alkoxy or trifluoromethyl; or a pharmaceutically acceptable salt thereof; or a pharmaceutically acceptable prodrug ester thereof.

22. A method according to claim 20 in which the compound is
N-{4[3-(4-fluorobenzenesulfonyl)-4-hydroxyphenoxy]-3,5-dimethylphenyl}oxamic acid;
or a pharmaceutically acceptable salt thereof; or a pharmaceutically acceptable prodrug ester thereof.

* * * * *